US010258424B2

(12) United States Patent
Bally

(10) Patent No.: US 10,258,424 B2
(45) Date of Patent: Apr. 16, 2019

(54) SACRIFICIAL MECHANICAL LINK

(71) Applicant: Nexxspan Healthcare, LLC, Lithia, FL (US)

(72) Inventor: Alexander Bally, Marston Mills, MA (US)

(73) Assignee: Nexxspan Healthcare, LLC, Lithia, FL (US)

( * ) Notice: Subject to any disclaimer, the term of this patent is extended or adjusted under 35 U.S.C. 154(b) by 382 days.

(21) Appl. No.: 15/049,466

(22) Filed: Feb. 22, 2016

(65) Prior Publication Data

US 2017/0241457 A1 Aug. 24, 2017

(51) Int. Cl.
| A61B 50/13 | (2016.01) |
| A61B 50/26 | (2016.01) |
| A61B 50/24 | (2016.01) |
| A61G 12/00 | (2006.01) |
| F16B 7/04 | (2006.01) |

(52) U.S. Cl.
CPC .............. *A61B 50/24* (2016.02); *A61B 50/13* (2016.02); *A61G 12/008* (2013.01); *A61B 50/26* (2016.02); *F16B 7/042* (2013.01)

(58) Field of Classification Search
CPC ......... A61B 50/13; A61B 50/15; A61B 50/24; A61B 50/26; A61B 2050/155; Y10T 403/11; Y10T 403/45; Y10T 403/55; Y10T 403/553; F16B 2012/403; F16B 7/00
See application file for complete search history.

(56) References Cited

U.S. PATENT DOCUMENTS

| 2,085,074 | A | * | 6/1937 | Boyles | ...................... E03B 9/02 |
| | | | | | 137/272 |
| 2,409,432 | A | | 10/1946 | Hubbard | |
| 2,460,244 | A | | 1/1949 | Strauss | |
| 3,570,376 | A | | 3/1971 | Overton | |
| 3,912,405 | A | * | 10/1975 | Katt | ........................ E01F 9/635 |
| | | | | | 403/11 |
| 4,214,685 | A | * | 7/1980 | Pletz | ......................... A45F 3/04 |
| | | | | | 224/634 |
| D262,237 | S | | 12/1981 | Stauber | |

(Continued)

FOREIGN PATENT DOCUMENTS

| EP | 3063454 | 9/2018 |
| NL | 2000571 | 10/2008 |
| WO | 2017147005 | 8/2017 |

OTHER PUBLICATIONS

Bally, Alexander; Issue Notification for U.S. Appl. No. 14/686,439, filed Apr. 14, 2015, dated Dec. 8, 2016, 1 pg.

(Continued)

*Primary Examiner* — Michael P Ferguson
(74) *Attorney, Agent, or Firm* — Taylor English Duma LLP

(57) ABSTRACT

A sacrificial mechanical link for linking a first mechanical element to a second mechanical element includes: a sacrificial element having a first end and a second end; and a first mechanical element removably connected to the first end of the sacrificial element. A method of using a sacrificial mechanical link includes: coupling a first mechanical element to a second mechanical element with a sacrificial element; and applying a force to a one of the first mechanical element and the second mechanical element to cause deformation of the sacrificial element.

19 Claims, 15 Drawing Sheets

(56) References Cited

U.S. PATENT DOCUMENTS

| | | | | |
|---|---|---|---|---|
| 4,367,871 | A | * | 1/1983 | Schiefer .............. A63B 49/035 403/294 |
| 4,511,158 | A | | 4/1985 | Varga et al. |
| 4,725,027 | A | | 2/1988 | Bekanich |
| 4,869,552 | A | * | 9/1989 | Tolleson ............... A47C 7/445 297/296 |
| 4,945,592 | A | | 8/1990 | Sims et al. |
| 5,160,111 | A | * | 11/1992 | Hugron ................. E01F 9/685 248/156 |
| D339,195 | S | | 9/1993 | Nash et al. |
| 5,306,109 | A | | 4/1994 | Kreuzer et al. |
| 5,366,191 | A | | 11/1994 | Bekanich |
| 5,474,408 | A | | 12/1995 | Dinitz |
| 5,527,125 | A | | 6/1996 | Kreuzer et al. |
| D381,745 | S | | 7/1997 | Owens |
| 5,797,613 | A | * | 8/1998 | Busby .................... B62K 19/18 267/30 |
| 5,865,456 | A | * | 2/1999 | Busby .................... B62K 19/18 267/30 |
| 5,898,961 | A | | 5/1999 | Ambach et al. |
| 6,042,292 | A | | 3/2000 | Belanger |
| 6,308,927 | B1 | * | 10/2001 | Leahy .................... E01F 9/635 248/530 |
| 7,065,812 | B2 | | 6/2006 | Newkirk et al. |
| 7,254,850 | B2 | | 8/2007 | Newkirk et al. |
| 7,258,310 | B2 | | 8/2007 | Norris |
| 7,314,200 | B2 | | 1/2008 | Bally |
| 7,418,749 | B2 | | 9/2008 | Graham et al. |
| 7,661,641 | B2 | | 2/2010 | Wong et al. |
| 7,676,865 | B2 | | 3/2010 | Graham et al. |
| 7,735,788 | B2 | | 6/2010 | Newkirk et al. |
| 7,748,672 | B2 | | 7/2010 | Walke |
| 7,789,361 | B2 | | 9/2010 | Bally et al. |
| 7,798,456 | B2 | | 9/2010 | Newkirk et al. |
| 7,845,601 | B1 | | 12/2010 | Culpepper et al. |
| 7,865,983 | B2 | | 1/2011 | Newkirk et al. |
| 7,980,533 | B1 | | 7/2011 | Anderson |
| 8,104,729 | B2 | | 1/2012 | Walke et al. |
| D655,408 | S | | 3/2012 | Bally |
| D655,409 | S | | 3/2012 | Bally |
| 8,579,244 | B2 | | 11/2013 | Bally |
| 9,404,616 | B2 | | 8/2016 | Bally |
| 9,528,536 | B2 | | 12/2016 | Bally |
| 9,816,663 | B2 | | 11/2017 | Bally |
| 9,827,062 | B2 | | 11/2017 | Bally |
| 2005/0253034 | A1 | | 11/2005 | Bally et al. |
| 2006/0179571 | A1 | | 8/2006 | Newkirk |
| 2006/0242763 | A1 | | 11/2006 | Graham et al. |
| 2006/0249641 | A1 | | 11/2006 | Bally et al. |
| 2007/0069093 | A1 | | 3/2007 | Graham et al. |
| 2007/0157385 | A1 | | 7/2007 | Lemire |
| 2007/0267550 | A1 | | 11/2007 | Blankenship et al. |
| 2008/0149788 | A1 | | 6/2008 | Wong et al. |
| 2008/0217910 | A1 | | 9/2008 | Walke et al. |
| 2009/0065668 | A1 | | 3/2009 | Walke |
| 2011/0217876 | A1 | | 9/2011 | Siebens |
| 2011/0272538 | A1 | | 11/2011 | Bally |
| 2013/0125367 | A1 | | 5/2013 | Rode |
| 2014/0048661 | A1 | | 2/2014 | Bally |
| 2014/0237721 | A1 | | 8/2014 | Lemire |
| 2016/0153611 | A1 | | 6/2016 | Bally |
| 2017/0049525 | A1 | | 2/2017 | Bally |
| 2017/0241461 | A1 | | 8/2017 | Bally |

OTHER PUBLICATIONS

Bally, Alexander; Applicant Initiated Interview Summary for U.S. Appl. No. 15/019,323, filed Feb. 9, 2016, dated Dec. 20, 2016, 3 pgs.

Bally, Alexander; Non-Final Office Action for U.S. Appl. No. 15/347,070, filed Nov. 9, 2016, dated Jan. 12, 2017; 17 pgs.

Bally, Alexander; Notice of Allowance for U.S. Appl. No. 14/686,439, filed Apr. 14, 2015, dated Aug. 15, 2016, 12 pgs.

Bally, Alexander; Non-Final Office Action for U.S. Appl. No. 15/019,323, filed Feb. 9, 2016, dated Oct. 18, 2016; 21 pgs.

Bally, Alexander; Notice of Allowance for U.S. Appl. No. 15/347,070, filed Nov. 9, 2016, dated Jul. 27, 2017, 17 pgs.

Bally, Alexander; Issue Notification for U.S. Appl. No. 13/104,531, filed May 10, 2011, dated Oct. 23, 2013, 1 pg.

Bally, Alexander; Non-Final Office Action for U.S. Appl. No. 13/104,531, filed May 10, 2011, dated Apr. 23, 2013, 15 pgs.

Bally, Alexander; Notice of Allowance for U.S. Appl. No. 13/104,531, filed May 10, 2011, dated Aug. 22, 2013, 12 pgs.

Bally, Alexander; Restriction Requirement for U.S. Appl. No. 13/104,531, filed May 10, 2011, dated Feb. 5, 2013, 6 pgs.

Bally, Alexander; U.S. Patent Application entitled: Secure Equipment Transfer System, having U.S. Appl. No. 13/104,531, filed May 10, 2011, 81 pgs.

Bally, Alexander; Final Office Action for U.S. Appl. No. 14/064,345, filed Oct. 28, 2013, dated Jul. 15, 2015, 9 pgs.

Bally, Alexander; Non-Final Office Action for U.S. Appl. No. 14/064,345, filed Oct. 28, 2013, dated Apr. 6, 2015, 14 pgs.

Bally, Alexander; Notice of Allowance for U.S. Appl. No. 14/064,345, filed Oct. 28, 2013, dated Nov. 9, 2015, 10 pgs.

Bally, Alexander; U.S. Continuation Application entitled: Secure Equipment Transfer System, having U.S. Appl. No. 14/064,345, filed Oct. 28, 2013, 89 pgs.

Bally, Alexander; Applicant-Initiated Interview Summary for U.S. Appl. No. 14/686,439, filed Apr. 14, 2015, dated Oct. 22, 2015, 3 pgs.

Bally, Alexander; Non-Final Office Action for U.S. Appl. No. 14/686,439, filed Apr. 14, 2015, dated Sep. 1, 2015, 20 pgs.

Bally, Alexander; U.S. Patent Application entitled: Secure Equipment Transfer System having U.S. Appl. No. 14/686,439, filed Apr. 14, 2015, 124 pgs.

Bally, Alexander; U.S. Patent Application entitled: Secure Equipment Transfer System having U.S. Appl. No. 15/019,323, filed Feb. 9, 2016, 76 pgs.

Bally, Alex; International Search Report and Written Opinion for PCT/US2013/067007, filed Oct. 28, 2013, dated Mar. 10, 2014, 8 pgs.

Bally, Alex; PCT Application entitled: Secure Equipment Transfer System, having serial No. PCT/US2013/067007, filed Oct. 28, 2013, 73 pgs.

Bally, Alex; International Search Report and Written Opinion for PCT Application No. PCT/US15/27300, filed Apr. 23, 2015, dated Sep. 1, 2015, 13 pgs.

Bally, Alex; PCT Application entitled: Secure Equipment Transfer System having serial No. PCT/US15/27300, filed Apr. 23, 2015, 125 pgs.

Bally, Alexander; Issue Notification for U.S. Appl. No. 29/393,210, filed Jun. 1, 2011, dated Feb. 15, 2012, 1 pg.

Bally, Alexander; Non-Final Office Action for U.S. Appl. No. 29/393,210, filed Jun. 1, 2011, dated Oct. 26, 2011, 7 pgs.

Bally, Alexander; Notice of Allowance for U.S. Appl. No. 29/393,210, filed Jun. 1, 2011, dated Nov. 23, 2011, 5 pgs.

Bally, Alexander; U.S. Design Application entitled: Symmetrical Transfer Device, having U.S Appl. No. 29/393,210, filed Jun. 1, 2011, 8 pgs.

Bally, Alexander; Issue Notification for U.S. Appl. No. 29/393,211, filed Jun. 1, 2011, dated Feb. 15, 2012, 1 pg.

Bally, Alexander; Non-Final Office Action for U.S. Appl. No. 29/393,211, filed Jun. 1, 2011, dated Oct. 25, 2011, 6 pgs.

Bally, Alexander; Notice of Allowance for U.S. Appl. No. 29/393,211, filed Jun. 1, 2011, dated Nov. 25, 2011, 5 pgs.

Bally, Alexander; U.S. Design Application entitled: Asymetrical Transfer Device, having U.S. Appl. No. 29/393,211, filed Jun. 1, 2011, 8 pgs.

Bally, Alexander; U.S. Provisional Patent Application Entitled: Secure Equipment Transfer System, U.S. Appl. No. 61/332,918, filed May 10, 2010; 63 pgs.

IMEC-TRUMPF North America, article located at <www.us.trumpf.com/products/,,,/imec.html>, accessed on Sep. 1, 2010, 1 pg.

Bally, Alexander; Final Office Action for U.S. Appl. No. 15/019,323, filed Feb. 9, 2017, dated Apr. 26, 2017, 18 pgs.

(56) References Cited

OTHER PUBLICATIONS

Bally, Alexander; Notice of Allowance for U.S. Appl. No. 15/019,323, filed Feb. 9, 2016, dated Jul. 7, 2017, 12 pgs.
Bally, Alex; First Examination Report for Australia Serial No. 2013404103, filed Oct. 28, 2013, dated Jun. 9, 2017, 3 pages.
Bally, Alex; Extended European Search Report for serial No. 13896274.1, filed Oct. 28, 2013, dated Apr. 24, 2017, 6 pgs.
Bally, Alexander; International Search Report and Written Opinion for PCT Application No. PCT/US17/18300, filed Feb. 17, 2017, dated Jun. 26, 2017, 14 pgs.
Bally, Alexander; Invitation to Pay Additional Fees for PCT Application No. PCT/US17/18300, filed Feb. 17, 2017, dated May 3, 2017, 3 pgs.
Bally, Alexander; Issue Notification for U.S. Appl. No. 14/064,345, filed Oct. 28, 2013, dated Feb. 24, 2016, 1 pg.
Bally, Alexander; Notice of Allowance for U.S. Appl. No. 14/064,345, filed Oct. 28, 2013, dated Mar. 25, 2016, 10 pgs.
Bally, Alexander; Final Office Action for U.S. Appl. No. 14/686,439, filed Apr. 14, 2015, dated Mar. 31, 2016, 14 pgs.
Bally, Alexander; U.S Patent Application entitled: Transfer System With Sacrificial Mechanical Link having U.S. Appl. No. 15/049,477, filed Feb. 22, 2016, 57 pgs.
Bally, Alexander; Issue Notification for U.S. Appl. No. 15/019,323, filed Feb. 9, 2016, dated Oct. 25, 2017, 1 pg.
Bally, Alexander; Issue Notification for U.S. Appl. No. 15/347,070, filed Nov. 9, 2016, dated Nov. 8, 2017, 1 pg.
Bally, Alex; International Preliminary Report on Patentability for PCT Application No. PCT/US15/27300, filed Apr. 23, 2015, dated Oct. 26, 2017, 10 pgs.
Bally, Alexander; Issue Notification for U.S. Appl. No. 14/064,345, filed Oct. 28, 2013, dated Jul. 13, 2016, 1 pg.
Bally, Alexander; Advisory Action for U.S. Appl. No. 14/686,439, filed Apr. 14, 2015, dated Jul. 11, 2016, 3 pgs.
Bally, Alexander; Applicant Initiated Interview Summary for U.S. Appl. No. 14/686,439, filed Apr. 14, 2015, dated Jun. 17, 2016, 3 pgs.
Bally, Alex; International Preliminary Report on Patentability for PCT/US2013/067007, filed Oct. 28, 2013, dated May 3, 2016, 6 pgs.
Bally, Alexander; Requirement for Restriction/Election for U.S. Appl. No. 15/049,477, filed Feb. 22, 2016, dated May 14, 2018, 6 pgs.
Bally, Alexander; Applicant-Initiated Interview Summary for U.S. Appl. No. 15/049,477, filed Feb. 22, 2016, dated Oct. 15, 2018, 3 pgs.
Bally, Alexander; Non-Final Office Action for U.S. Appl. No. 15/049,477, filed Feb. 22, 2016, dated Aug. 27, 2018, 57 pgs.
Bally, Alexander; Notice of Allowance for U.S. Appl. No. 15/049,477, filed Feb. 22, 2016, dated Dec. 4, 2018, 16 pgs.
Bally, Alex; Partial European Search Report for serial No. 15889408.9, filed Apr. 23, 2015, dated Oct. 25, 2018, 11 pgs.
Bally, Alexander; International Preliminary Report on Patentability for PCT Application No. PCT/US17/18300, filed Feb. 17, 2017, dated Sep. 7, 2018, 11 pgs.

* cited by examiner

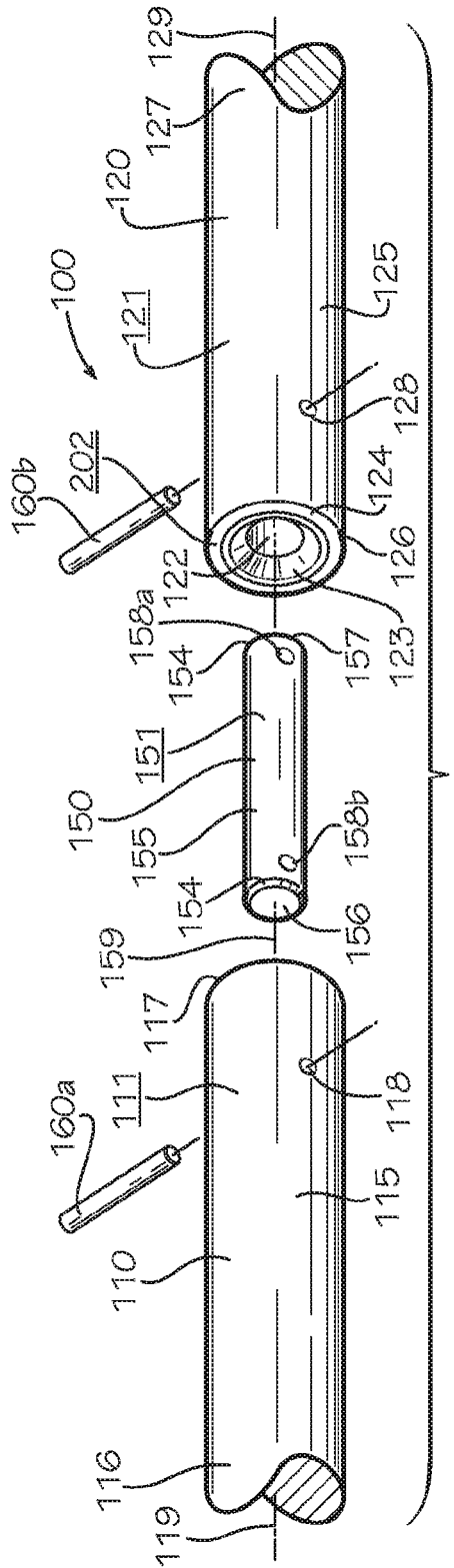
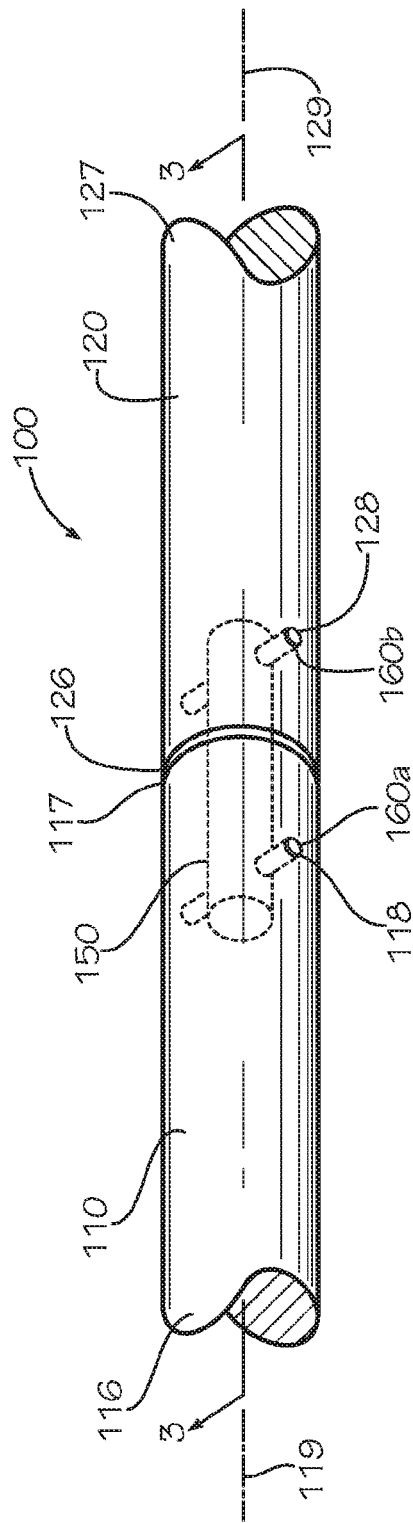
FIG. 1
FIG. 2

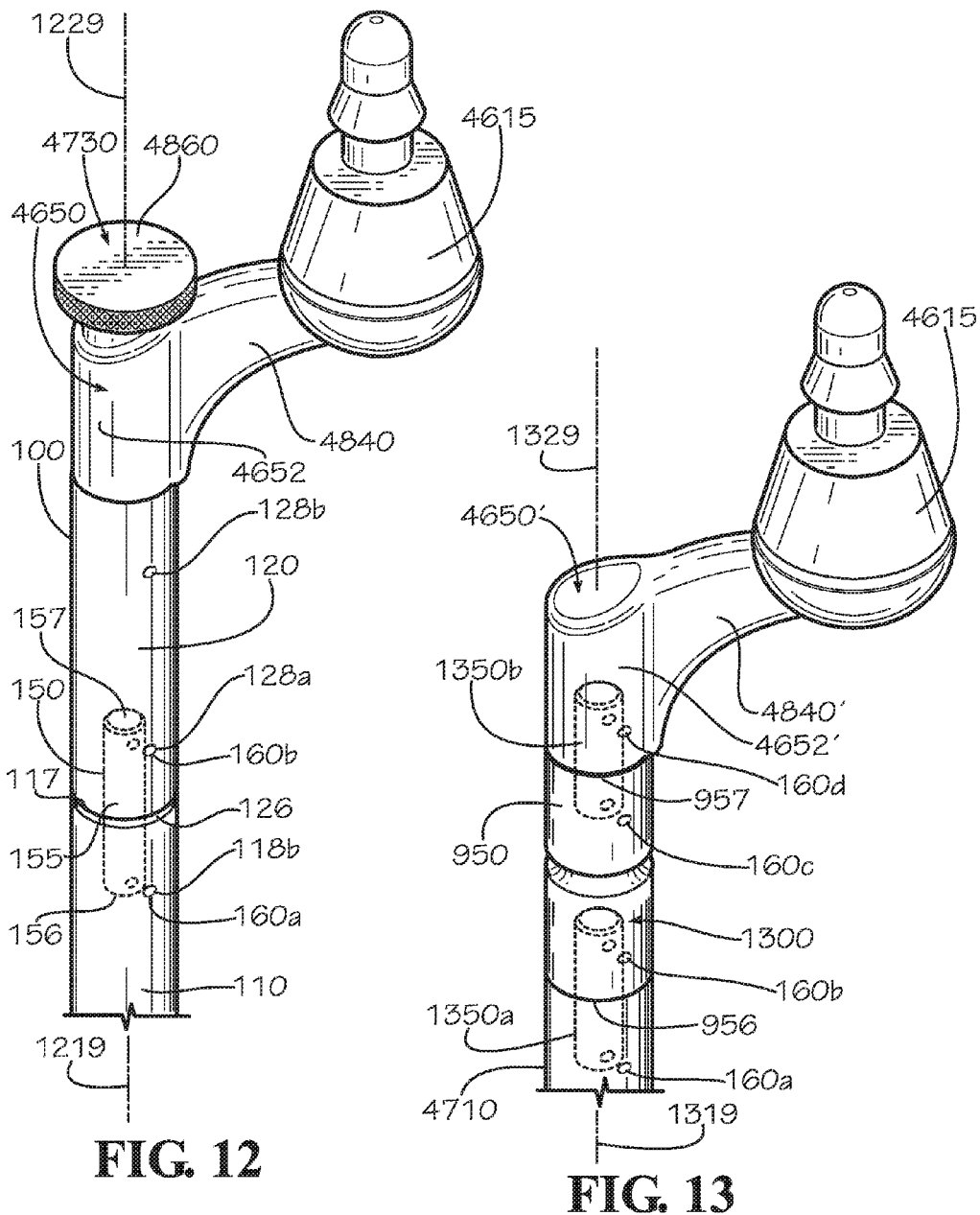

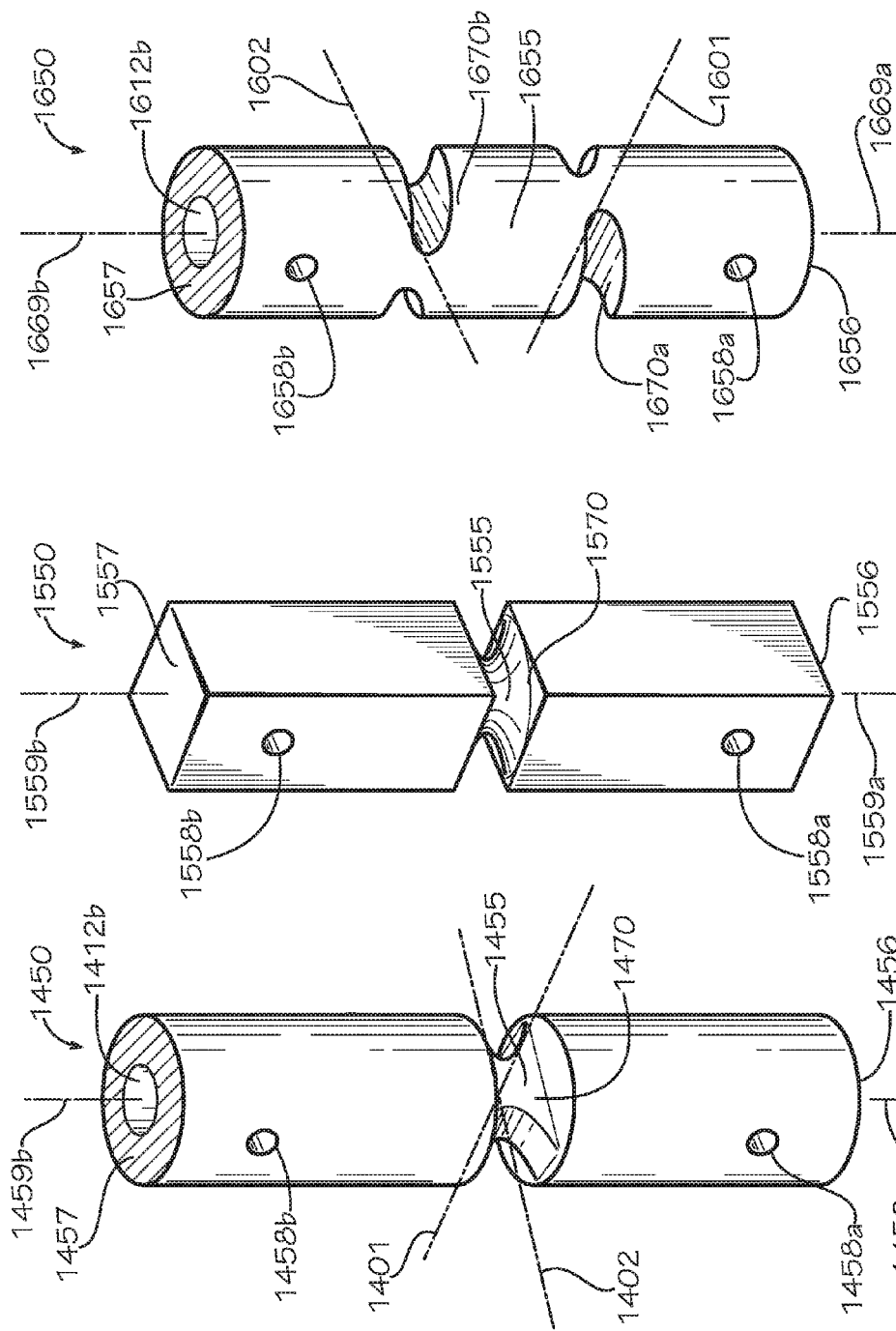

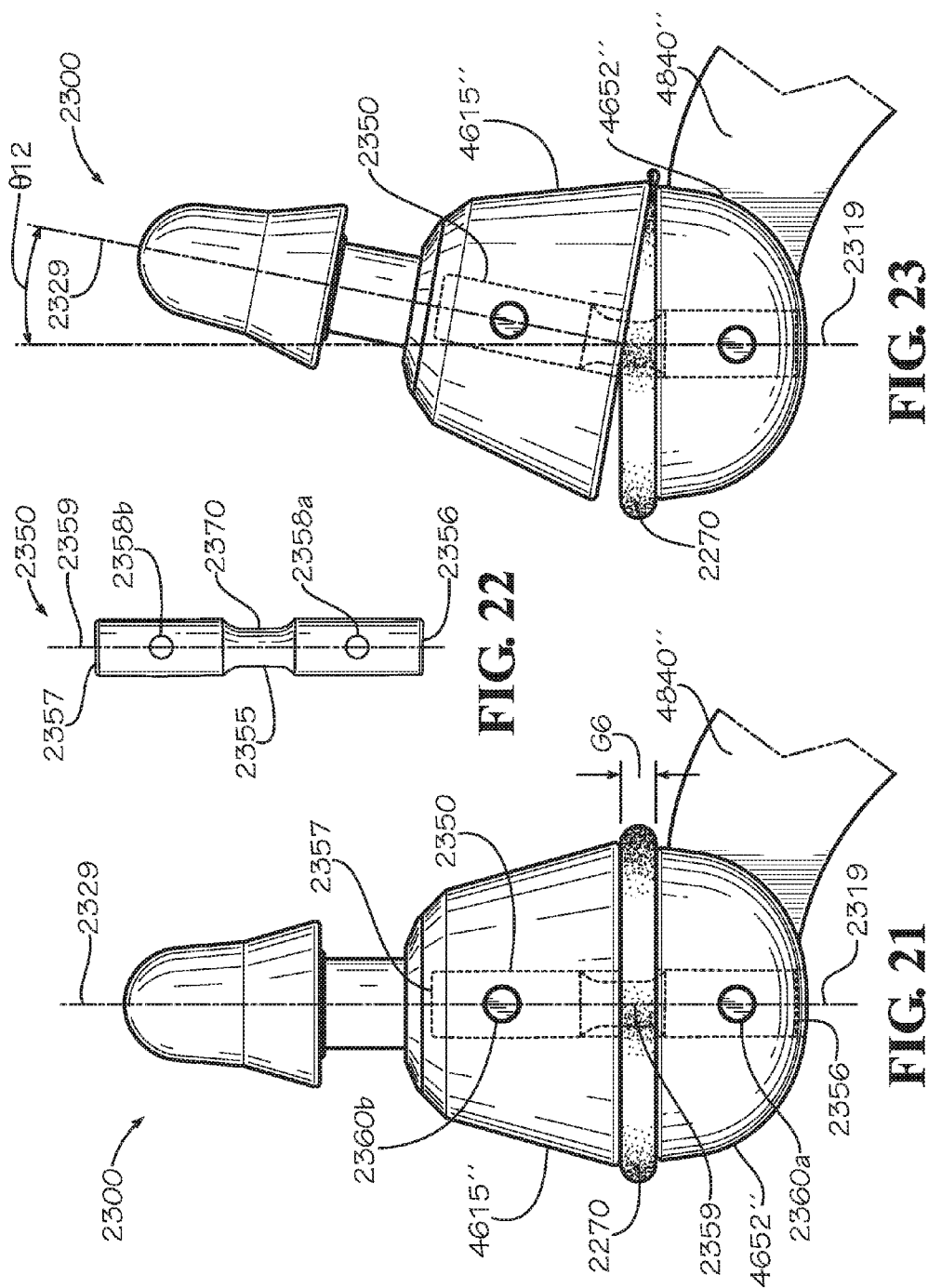

SACRIFICIAL MECHANICAL LINK

FIELD OF USE

This disclosure relates to mechanical linkages. More specifically, this disclosure relates to sacrificial mechanical linkages or links that connect portions of a structural support system.

RELATED ART

Structural support systems that support the weight of equipment, which can include, for example and without limitation, medical equipment in a health care delivery environment, are often made of lightweight structural members to minimize the weight of such systems and to reduce the cost of manufacturing, installing, and using such systems. In a health care delivery environment, medical equipment can typically be set up at a patient's bedside where it can be supported by various stands, racks, or hangers.

In operation, when equipment such as medical equipment is transported from one location to another in an emergency, equipment or structural support systems supporting the equipment can come into contact with neighboring structures and encounter structural loads that can damage the equipment or the structural support systems supporting the equipment. If the encountered structural loads are sufficiently great, the equipment or the structural support systems can be weakened or damaged. Critical equipment or the structural support systems supporting the equipment can be at risk for premature, catastrophic failure having potentially serious consequences for health care providers and their patients.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, disclosed is a sacrificial mechanical link for linking a first mechanical element to a second mechanical element. In this aspect, the link can comprise a sacrificial element having a first end and a second end and a first mechanical element configured to be removably connected to the first end of the sacrificial element.

As one skilled in the art will appreciate, in an electrical system or electrical circuit, it is conventional to install a fuse to protect critical components in the circuit from electrical overload. However, in a mechanical system, the concept of such an exemplary fuse is largely foreign. For various reasons, a mechanical system and particularly a load-bearing structure is typically designed to handle—without failure— the greatest load that it might reasonably be expected to experience during its life cycle. For example, an automobile is designed for safety reasons to fail in certain "crumple zones" to protect the vehicle's occupant and the designed-to-fail parts are typically replaceable such that the vehicle can be re-used. A vehicle whose crumple zone is loaded by either static or dynamic forces beyond which it's body structure was designed to handle without deformation must either be pulled or stretched back into shape—if the damage is minor, or it must have damaged sections mechanically cut out and new sections welded in by skilled craftsman, or it must simply be scrapped.

In a health care delivery environment, various pieces of patient support equipment are assembled together and lifted, lowered, transported, or otherwise manipulated in the course of caring for patients. The patient support equipment can be supported by five-star floor stands, attached to headwalls, suspended from booms that are affixed to a ceiling, floor-mounted or wall-mounted columns, or on other stationary or mobile platforms. These various pieces of equipment can be specified, designed, and manufactured by different equipment vendors, and the weakest point in each system or subsystem—whether it be a hospital bed or a transfer system or some other piece of equipment—is routinely not the easiest or least expensive component to repair and can experience failure without notice to the user.

In mechanical systems, incorporating a mechanical "fuse" or sacrificial mechanical element protects mechanical or structural components in a system—in a predictable and visible manner—from structural loading beyond which the structural components were designed to handle. Failure of the sacrificial mechanical element is acceptable and even preferred because the cost to replace the sacrificial mechanical element is lower than the cost to replace the more expensive components (whether those more expensive components are part of a mechanical system or electrical system or other systems). Many applications for such a sacrificial mechanical element exist across various industries, including wherever systems utilize structural components to support structural loads.

While not limited to use in any one type of system and certainly not limited to use only in a medical environment such as a hospital, a sacrificial mechanical element can be used to protect expensive medical equipment from damage caused during operation or transport of the equipment. For example, medical personnel in a high-pressure environment can be required to quickly move patients being supported by medical equipment such as hospital beds and intravenous (IV) poles to surgery or to move equipment to patients or to otherwise transport equipment around the medical environment. When a hospital bed or other medical support platform comprises a transfer system for docking and supporting medical equipment and one or more components of the larger system including the transfer system are able to be raised or lowered, exchanged with shorter or taller or narrower or wider equipment, it is possible for even skilled personnel to run an extended IV pole supported by a transfer system into doorframes and other overhead obstacles. Also, medical care staff and cleaning staff can pull or push a bed by holding onto one or more parts of a transfer system that were not designed for such loading. As a result, the vertical position of the transfer device or some functional aspect of the transfer system or a connecting system is adversely affected—including, but not limited to, bending of a hospital bed frame or bending of a bed post to which a transfer device is attached to the bed. The adverse effects can lead to malfunctions during docking of one portion of a transfer system to another.

A "fuse" element or sacrificial mechanical link can be installed in a bed post or elsewhere in a transfer assembly. The sacrificial mechanical link becomes the "weakest link in the chain" so that any structural overloading is concentrated in and is allowed to affect a visible, easily localized, and repairable "sacrificial" element. This sacrificial element is designed to deform under a load that will not damage the transfer system's integrity, thus protecting the other components of the transfer system.

In a further aspect, a method of using a sacrificial mechanical link is provided that comprises: coupling a first mechanical element to a second mechanical element with a sacrificial element; and applying a force to a one of the first mechanical element and the second mechanical element to cause deformation of the sacrificial element.

Various implementations described in the present disclosure can include additional systems, methods, features, and advantages, which can not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations may be realized and obtained by means of the systems, methods, features particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate several aspects of the invention and together with the description, serve to explain various principles of the invention. Corresponding features and components throughout the figures can be designated by matching reference characters for the sake of consistency and clarity.

FIG. 1 is an exploded perspective view of a sacrificial mechanical link in accordance with one aspect of the current disclosure.

FIG. 2 is a perspective view of the sacrificial mechanical link of FIG. 1 in an assembled state.

FIG. 12 is a perspective view of a receiver arm of a transfer device including the sacrificial mechanical link of FIG. 1 in accordance with one aspect of the current disclosure.

FIG. 13 is a perspective view of a receiver arm of a transfer device including the sacrificial element of FIG. 10 in accordance with one aspect of the current disclosure.

FIG. 14 is a perspective view of a sacrificial element in accordance with yet another aspect of the current disclosure.

FIG. 15 is a perspective view of a sacrificial element in accordance with yet another aspect of the current disclosure.

FIG. 16 is a perspective view of a sacrificial element in accordance with yet another aspect of the current disclosure.

FIG. 21 is a detail side view of a sacrificial mechanical link installed in a receiver arm of a transfer system in accordance with another aspect of the current disclosure.

FIG. 22 is a detail side view of a sacrificial element of the sacrificial mechanical link of FIG. 21.

FIG. 23 is a detail side view of the sacrificial mechanical link of FIG. 22 in a deformed state.

DETAILED DESCRIPTION

Figure 3A:
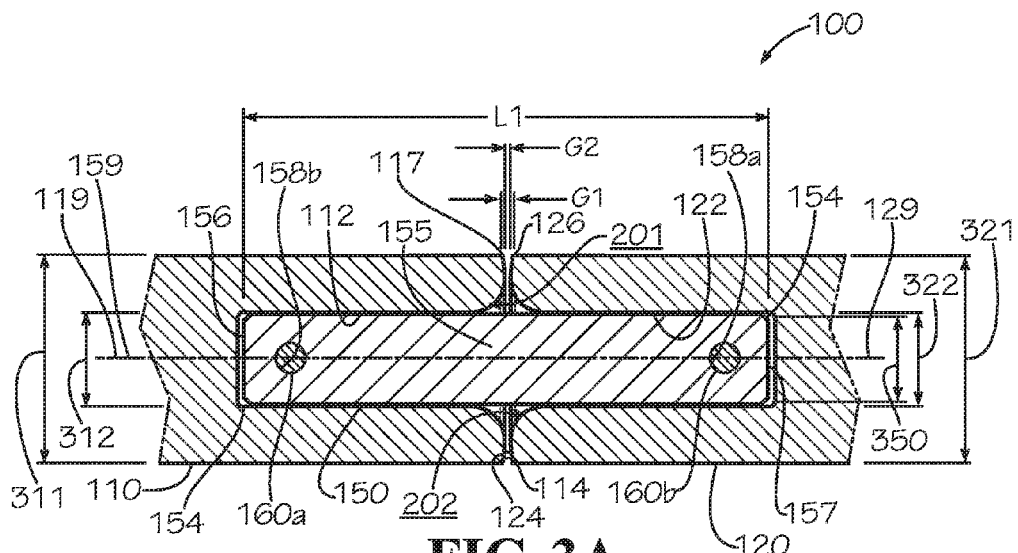
FIG. 3A is a detail sectional view of the sacrificial mechanical link of FIG. 1 taken along line 3-3 of FIG. 2.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the one aspect of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a sacrificial element" can include two or more such sacrificial elements unless the context indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For purposes of the current disclosure, a material property or a dimension measuring about X on a particular measurement scale measures within a range between X plus an industry-standard upper tolerance for the specified measurement and X minus an industry-standard lower tolerance for the specified measurement. Because tolerances can vary between different components, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list.

In one aspect, a sacrificial mechanical link and associated methods, systems, devices, and various apparatus are described herein. In one aspect, the sacrificial mechanical link can comprise a sacrificial element. In a further exemplary aspect, of a sacrificial mechanical link, a ductile (i.e., non-brittle) rod or pin is installed between the two parts of a cut post, such as a bed post. In this example, when a portion of the transfer system such as an IV pole is subjected to excessive force, the sacrificial element bends until the two edges of the cut bed post come into contact. Bending the sacrificial element requires mechanical energy and can help to not only to absorb the overloading force but to visually notify personnel of the overloading. Deformation of the exemplary IV pole can be limited in such a way that the current task can still be completed. Moreover, the deformed sacrificial link results in a clearly visible tilt of one portion of the system with respect to another part of the transfer system and visually signals users to take the system out of operation until it can be repaired. It is contemplated that a repair can be accomplished by removing the deformed sacrificial element and replacing it with a new sacrificial element. The more expensive components such as the sophisticated medical equipment supported by the transfer system and critical IV lines and hoses and other apparatuses for supporting the patient, will not be damaged as a result of the sacrificial deformation of the sacrificial element.

Figure 17A:
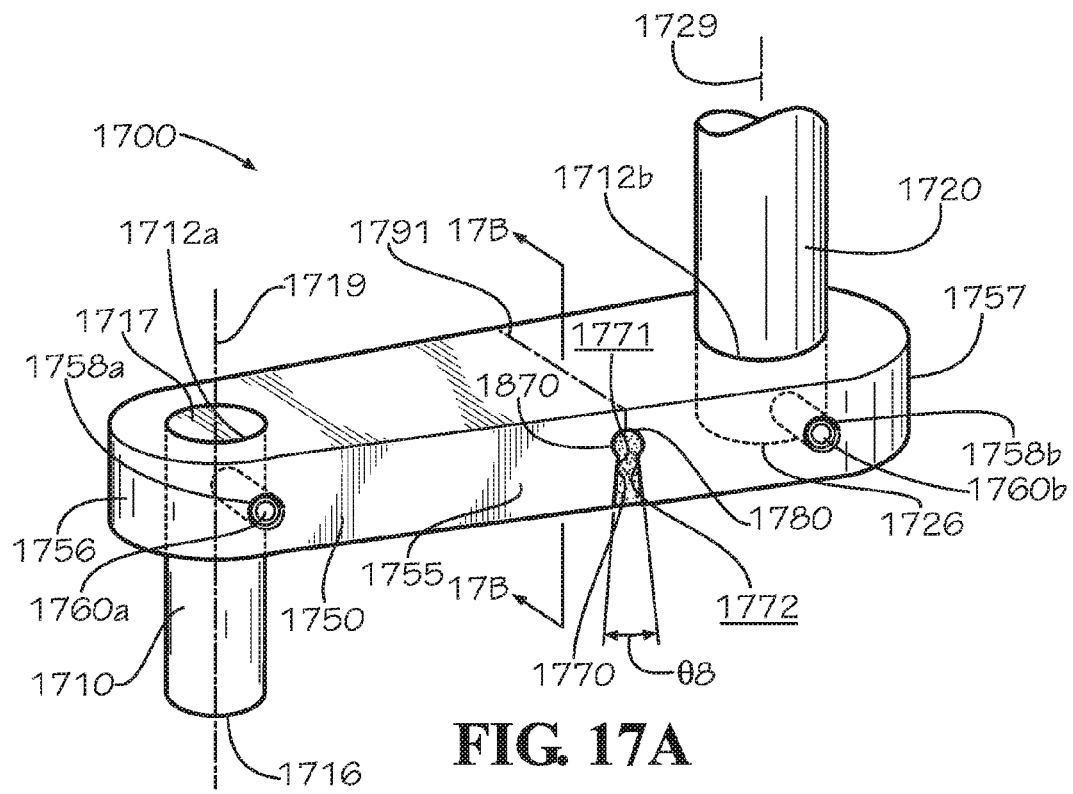
FIG. 17A is a perspective view of a sacrificial mechanical link in a non-deformed state in accordance with yet another aspect of the current disclosure.
Figure 17B:
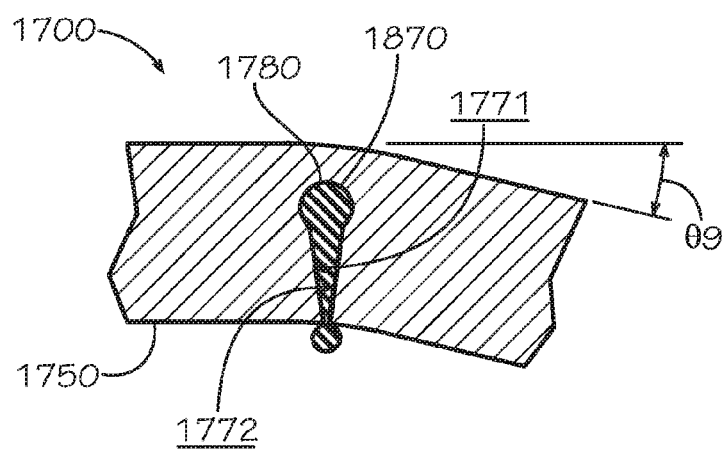
FIG. 17B is a side view of the sacrificial mechanical link of FIG. 17A in a deformed state taken along line 17B-17B of FIG. 17A.

In one aspect and as shown in FIG. 1, a sacrificial mechanical link 100 can comprise a sacrificial element 150, a first mechanical element 110, and a second mechanical element 120. The disclosure of the sacrificial element 150, the first mechanical element 110, and the second mechanical element 120 should not be considered limiting on the current disclosure, however, as in one aspect a second mechanical element may not be required. In one aspect, a central axis 159 of the sacrificial element 150 can be aligned with a central axis 119 of the first mechanical element 110 or with a central axis 129 of the second mechanical element 120 or with both the central axis 119 and the central axis 129. In another aspect, the sacrificial element 150 can be configured to link the first mechanical element 110 to the second mechanical element 120 and can be configured to be removably connected to the first mechanical element 110 and to the second mechanical element 120. In one aspect, the sacrificial element 150 can be sized to be received within either the first mechanical element 110 or the second mechanical element 120. In another aspect, the sacrificial element 150 can be sized to be assembled to the outside of the first mechanical element 110 or the second mechanical element 120 (as shown, for example and without limitation, in the sacrificial mechanical link 1700 of FIGS. 17A and 17B showing a sacrificial element 1750 assembled to the outside of a first mechanical element 1710 and a second mechanical element 1720).

In one aspect, the sacrificial element 150 can comprise a first end 156, a second end 157, and a central portion 155. In this aspect and as shown in FIG. 3A, the sacrificial element 150 can define a length L1, a diameter 350, an outer surface 151, a chamfered edge 154 at each of the first end 156 and the second end 157, and a pair of attachment bores 158a,b. In one aspect, the attachment bore 158b can be proximate the first end 156 and the attachment bore 158a is proximate the second end 157. In another aspect, the central portion 155 is that portion of the sacrificial element 150 can be between the attachment bore 158a and the attachment bore 158b.

Figure 3B:
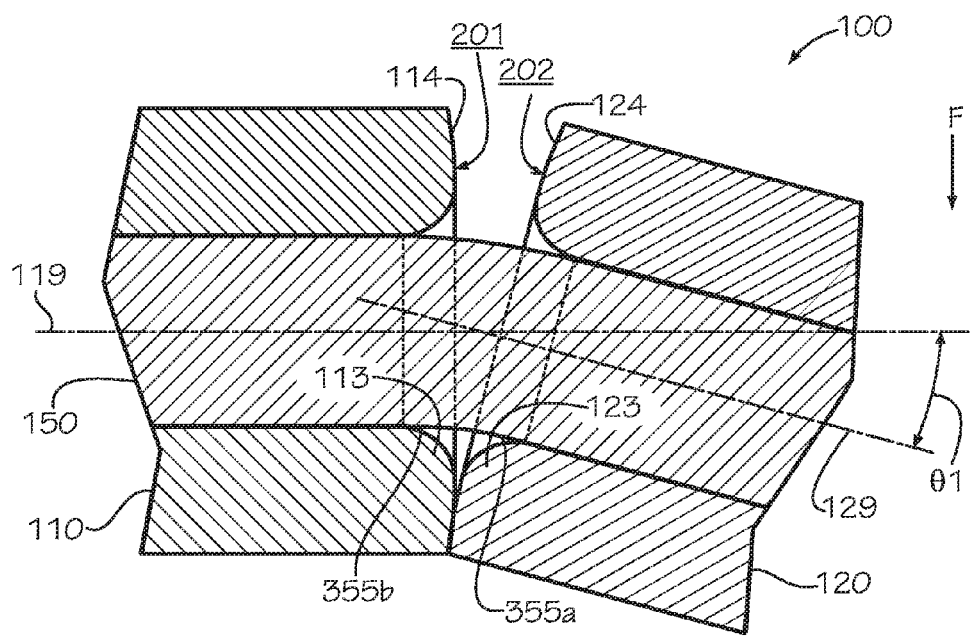
FIG. 3B is a detail sectional view of the sacrificial mechanical link of FIG. 1 in a deformed state.

In another aspect, the first mechanical element 110 can comprise a first end 116, a second end 117—which can extend any desirable distance from the first end 116—and a central portion 115. In this aspect and as shown in FIG. 3A, the first mechanical element 110 defines a main bore 112 extending from the second end 117, an outer diameter 311, an inner diameter 312, an outer surface 111, a chamfered edge 114 at the second end 117, and an attachment bore 118 proximate to the second end 117. In another aspect, the first mechanical element 110 can define an end cavity 113 in the second end 117 of the first mechanical element 110. In one aspect, as shown in FIG. 3A, the first mechanical element 110 can define an end surface 201 at the second end 117 of the first mechanical element 110, which in turn defines the end cavity 113. In another aspect, the end cavity 113 can be positioned axially inward from an axially outermost portion of the end surface 201 of the second end 117 of the first mechanical element 110. In an exemplary aspect, the end cavity 113 can be configured to form a radius at the intersection of the main bore 112 and the end surface 201. In another aspect and as shown in FIG. 3B, the first mechanical element 110 can be configured to comprise a stop, such as, for example and without limitation, the chamfered edge 114, which limits movement of the second mechanical element 120 relative to the first mechanical element 110 past a maximum deformation angle θ1 when overloading of the sacrificial mechanical link 100 causes movement of the second mechanical element 120 relative to the first mechanical element 110.

In one aspect, the second mechanical element 120 can comprise a first end 126, a second end 127—which can extend any desirable distance from the first end 126—and a central portion 125. In this aspect and as shown in FIG. 3A, the second mechanical element 120 can define a main bore 122 extending from the first end 126, an outer diameter 321, an inner diameter 322, an outer surface 121, a chamfered edge 124 at the first end 126, and an attachment bore 128 proximate to the first end 126. In this aspect, the second mechanical element 120 can define an end cavity 123 in the respective first and second ends 126,127 of the second mechanical element. In a further aspect, the second mechanical element 120 can define end surface 202 at the first end 126 of the second mechanical element 120, which in turn can define the end cavity 123. In one aspect, the end cavity 123 can be positioned axially inward from an axially outermost portion of the end surface 202 of the first end 126. In this aspect, it is contemplated that the end cavity 123 can form a radius at the intersection of the main bore 122 and the end surface 202. In yet another aspect, the second mechanical element 120 can comprise a stop, such as, for example and without limitation, the chamfered edge 124, which limits further movement of the first mechanical element 110 relative to the second mechanical element 120 past the maximum deformation angle θ1 when overloading of the sacrificial mechanical link 100 causes movement of the first mechanical element 110 relative to the second mechanical element 120.

In another aspect, the first mechanical element 110 and the second mechanical element 120 can be cylindrically shaped. Similarly, the sacrificial element 150 can be cylindrically shaped. However, it is contemplated that the cylindrical shape for the first mechanical element 110, the second mechanical element 120, and the sacrificial element 150 are exemplary and should not be considered limiting on the current disclosure.

In one aspect, the first end 156 of the sacrificial element 150 can be removably connected to the second end 117 of the first mechanical element 110 by axially aligning the attachment bore 158b with the attachment bore 118 and inserting a connecting fastener 160a, such as, for example and without limitation, a round pin, in the attachment bore 158b and in the attachment bore 118. In a similar aspect, it is contemplated that the second end 157 of the sacrificial element 150 can be removably connected to the first end 126 of the second mechanical element 120 by axially aligning the attachment bore 158a with the attachment bore 118 and inserting a connecting fastener 160b, such as, for example and without limitation, a round pin, in the attachment bore 158a and in the attachment bore 128a.

In one exemplary aspect, the connecting fasteners 160a,b can be round roller pins that can be configured to be conventionally driven into the attachment bores 118,128,158 with a round punch or other tool. Optional, connecting fasteners 160a,b, for example and without limitation, can comprise a solid pin, a threaded bolt or screw, a pin such as a clevis pin incorporating a head and defining a bore sized to receive a split pin or cotter pin, fasteners having a square or other polygonal cross-sectional shape, and the like. In another aspect, the sacrificial element 150 can be removably connected to the first mechanical element 110 and/or the second mechanical element 120 by threading the sacrificial element 150 into the second end 117 of the first mechanical element 110 or the first end 126 of the second mechanical element 120, and in such case the main bores 112,122 can also be threaded to match.

In a further aspect, an exemplary sacrificial mechanical link 100 is shown in an assembled state in FIG. 2. In one aspect, the first end 156 of the sacrificial element 150 can be installed in the main bore 112 at the second end 117 of the first mechanical element 110 and, similarly, the second end 157 of the sacrificial element 150 can be installed in the main bore 122 at the first end 126 of the second mechanical element 120. The connecting fastener 160a is shown installed in attachment bore 158b and the attachment bore 118 and, similarly, the connecting fastener 160b is shown installed in both the attachment bore 158a and the attachment bore 128. In one aspect, the second end 157 and the first end 156 of the sacrificial element 150 is respectively held firmly within the main bores 112,122 so that the sacrificial element 150 does not rotate within the main bores 112,122 about axes 119,129 and so that the sacrificial element 150 does not pull out of the main bores 112,122 and so that the sacrificial element 150 is positioned accurately and consistently within the main bores 112,122. In another aspect, the second end 157 and the first end 156 of the sacrificial element 150 is respectively held firmly within the main bores 112,122 so that the sacrificial element 150 is positioned accurately and consistently within the main bores 112,122 and precisely aligns the first mechanical element 110 with the second mechanical element 120.

In a further aspect, the exemplary sacrificial mechanical link 100 is shown in a non-deformed, assembled state in FIG. 3A. In this aspect, when the connecting fastener 160a is installed in the attachment bores 118,158b and the connecting fastener 160b is installed in the attachment bores 128,158a, the end surface 201 of the first mechanical element 110 and the end surface 202 of the second mechanical element 120 can define a gap distance G1 between radially outermost edges of each and a gap distance G2 between axially outermost portions of each. Optionally, the gap distance G1 can be larger than the gap distance G2 or the gap distance G1 can be substantially equal to the gap distance G2. In one aspect, the axis 159 of the sacrificial element 150 can be aligned with the axis 119 of the first mechanical element 110 and with the axis 129 of the second mechanical element 120.

In a further aspect, the exemplary sacrificial mechanical link 100 is shown in a deformed, assembled state in FIG. 3B. One skilled in the art will appreciate that any force, such as the exemplified F, that could be mechanically or otherwise dynamically applied to second mechanical element 120 could cause the sacrificial element 150 to experience internal stresses beyond the elastic limit of a material thus causing the sacrificial element 150 to deform where it is unsupported in the central portion 155. In the exemplified and non-limiting illustrated application of force F in FIG. 3B that acts in a direction normal or orthogonal to the axis 129 of the second mechanical element 120 causes stress in the sacrificial element 150 because the force F acts at a distance from the sacrificial element 150 resulting in an applied leverage and/or a torque on the sacrificial element 150, where torque experienced at the sacrificial element 150 is a product of the force F and the distance between the sacrificial element 150 and the line through which the exemplified force F acts on the second element or on that which is connected to the second element. It is contemplated that the sacrificial element 150 is deformable in any horizontal direction between zero and 360 degrees, inclusive, when the axis 159 of the sacrificial element 150 is oriented along a substantially vertical axis.

In another aspect, the sacrificial element 150, at least in part, can be made from a different material than that of the first mechanical element 110 or the second mechanical element 120. Optionally, it is contemplated that a yield strength of a material forming the sacrificial element 150 can be lower than a yield strength of a material forming the first mechanical element 110 and/or of a material forming the second mechanical element 120. In another optional aspect, it is contemplated that the yield strength of a material forming the sacrificial element 150 can be substantially equal to or greater than a yield strength of a material forming the first mechanical element 110 or a yield strength of a material forming the second mechanical element 120. In this aspect, the sacrificial element 150 can be configured to deform without deformation of the first mechanical element 110 or the second mechanical element 120 by selectively dimensionally sizing the first mechanical element 110 and the second mechanical element 120 such that the sacrificial element would deformably fail prior to the respective first and second mechanical elements.

In one aspect, the factors determining how much the sacrificial element 150 bends include the following characteristics of either the sacrificial mechanical link 100 or the sacrificial element 150:

the elastic modulus, yield strength, and ultimate strength of the material of the sacrificial element 150;
the outside diameter of the sacrificial element 150;
the inside diameter of the main bores 112,122;
the gaps G1,G2 between the first mechanical element 110 and the second mechanical element 120;
the distance between the end surfaces 201,202 and a first point of contact on the sacrificial element 150, including the size of the radius or chamfer at the opening of the main bores 112,122; and
the angle and depth of the chamfered edges 114,124.

In one aspect, it is contemplated that a sufficiently high force F can cause the chamfered edge 114 of the first mechanical element 110 to contact the chamfered edge 124 of the second mechanical element 120 on a side opposite the side on which the force F acts. In this aspect, each of the chamfered edges 114,124 of the respective end surfaces 201,202, can function as a stop to prevent further movement of the chamfered edge 114 with respect to the chamfered edge 124 and therefore also can prevent further movement of the first mechanical element 110 with respect to the second mechanical element 120.

In another aspect, the axis 119 of the first mechanical element 110 and the axis 129 of the second mechanical element 120 can define a maximum deformation angle θ1 between the respective axes 119,129 when the sacrificial mechanical link 100 is in a deformed state. In this aspect, it is contemplated that the maximum deformation angle θ1 can be at least 1°, at least 2°, at least 3°, at least 4°, or at least 5°. Optionally, the maximum deformation angle θ1 can be between about 0.5° to about 25°, or between about 1° to about 15°. As contemplated and described below, obvious bending or tilting of the second mechanical element 120 with respect to the first mechanical element 110 is not required to notify the user that the sacrificial mechanical link 100 has been overloaded because another other methods of "failure" indication can be provided. It is contemplated that other exemplary methods of indication comprise but are not limited to, light indications and other visual indications, such as the displacement of a component of the sacrificial mechanical link 100 that does not require obvious bending of the second mechanical element 120 with respect to the first mechanical element 110.

In one aspect, the definition of the end cavity 113 in the first mechanical element 110 and the definition of the end cavity 123 in the second mechanical element 120 can facilitate deformation of the sacrificial element 150 by providing a space for the central portion 155 of the sacrificial element 150 to freely deform. In a further aspect, the shape of the end cavity 113 of the first mechanical element 110 or the end cavity 123 of the second mechanical element 120 can be configured to reduce or eliminate localized stresses where the sacrificial element 150 enters the main bore 112 of the first mechanical element 110 or the main bore 122 of the second mechanical element 120. In another aspect, as shown, an entrance to the main bores 112,122 can be formed to incorporate a radiused edge. In one aspect, the end cavities 113,123 that can be defined at an entrance to the main bores 112,122, respectively, can form a chamfered edge at the entrance with a chamfer angle of substantially 45°. It is also contemplated that the respective entrances to the main bores 112,122 can comprise an edge that is neither radiused nor chamfered.

In one aspect, a common sacrificial element 150 can be used in multiple joints and the size and shape of the end surface 201 in the first mechanical element 110 and the end surface 202 in the second mechanical element 120, including the size and shape of the end cavities 113,123 or the gap distances G1,G2 in one aspect, can be selectively adjusted to achieve similar deformation as with a sacrificial element 150 made from a different material or having a different size or shape. For example and without limitation, by decreasing the size of the gap distances G1,G2 and/or by reducing an axial dimension 410 of the end cavities 113,123 from a first sacrificial mechanical link 100 to a second mechanical link 100, additional surface area of the outer surface 151 of the sacrificial element 150, and specifically in the central portion 155, can be additional supported and the sacrificial element 150 can be restrained in such a way as to prevent deformation that would otherwise occur under a given force. In this aspect and as shown in FIG. 3B, a portion 355b of the outer surface 151 of the sacrificial element 150 can be left unsupported by the first mechanical element 110 due to the inclusion of the end cavity 113, and a portion 355a of the outer surface 151 of the sacrificial element 150 can be left unsupported by the second mechanical element 120 due to the inclusion of the end cavity 123. Optionally, a plurality of differing deformation responsive sacrificial elements 150 can be provided for service replacement which allows the user to elect to use an appropriately responsive sacrificial elements for the particular use.

Figure 4:
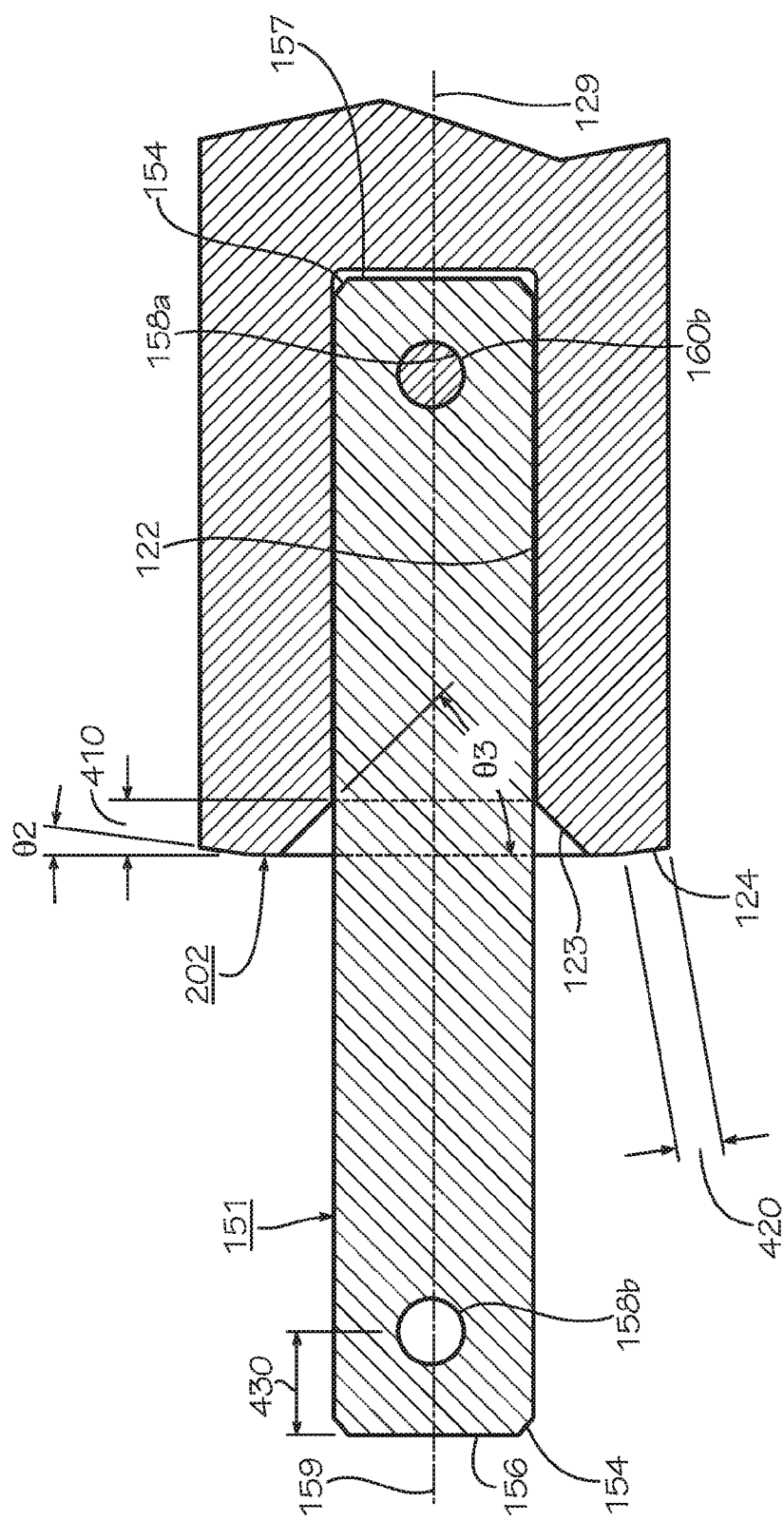
FIG. 4 is a detail sectional view of the sacrificial mechanical link of FIG. 1 without the first mechanical element 110 in accordance with another aspect of the current disclosure.

Referring to FIG. 4, in operation, the chamfered edges 154 and the end cavities 113,123 (end cavity 113 shown as a chamfered edge and end cavity 123 not shown) can ease the insertion of the sacrificial element 150 into the main bore 112 of the first mechanical element 110 or the main bore 122 of the second mechanical element 120. In one aspect, the sacrificial element 150 can be configured to be selectively removed and reinserted into the main bore 112 of the first mechanical element 110 or the main bore 122 of the second mechanical element 120 to form a tight, friction fit without the use of special tools. In this aspect, the friction fit can formed by conventionally manufacturing processing to ensure the proper tolerancing of the respective pieces such that the sacrificial element 150 has an external shape that conforms to the respective main bores 112,122. In another aspect, the friction fit can restrict or prevent the bending of the axis 159 of the sacrificial element 150 relative to the axis 119 of the first mechanical element 110 or the axis 129 of the second mechanical element 120 when the sacrificial element 150 is installed in the main bore 112 of the first mechanical element 110 or the main bore 122 of the second mechanical element 120.

In one aspect, the respective chamfered edges 114,124 of the respective first mechanical element 110 and the second mechanical elements 120 can define a chamfer angle θ2 relative to a cross-sectional plane extending perpendicular to the respective axis 119,129 of the first and second mechanical elements 110,120. In this aspect, the chamfer angle θ2 can measure about 40-60% of the maximum deformation angle θ1 of each of the respective first and second mechanical elements 110,120. In a further aspect, the end cavities 113,123 of the respective first and second mechanical elements 110,120 can define a chamfer angle θ3 relative to a cross-sectional plane extending perpendicular to the respective axis 119,129 of the first and second mechanical elements 110,120. In this aspect, the chamfer angle θ3 can measure substantially 45°. Optionally, the chamfer angle θ3 can measure more or less than 45°.

In a further aspect, when the sacrificial mechanical link 100 is in a deformed state and the chamfered edges 114,124 are in contact with one another, the pressure per unit area between the chamfered edges 114,124 can be selectively adjusted by increasing or decreasing the cross-sectional chamfer width 420. In one aspect, a center of the respective attachment bores 158a,b can be positioned an edge distance 430 away from the ends 157,156, which is sufficient to prevent tear-out of the attachment bores 158a,b. In one aspect, the connecting fasteners 160a,b have an outer diameter that is close enough to the inner diameter of the attachment bores 118,128,158 to fix the position of the sacrificial element 150 relative to the first mechanical element 110 and the second mechanical element 120.

In another aspect, a filler can be included in a sacrificial mechanical link. It is contemplated that very high forces can be transiently present between contact surfaces of the sacrificial mechanical link 100 such as, for example and without limitation, the chamfered edges 114,124 that are in contact with one other. In this aspect, the respective applied forces, acting on a portion of the system at a distance away and resulting in a lever arm geometry, are multiplied severalfold. In one aspect, the gap or gaps described by the gap distances G1,G2 can be filled at least partially with a filler material to prevent pinch points and to prevent the various fingers and other body parts, wires, IV lines, and contamination from filling those pinch points. In one aspect, gaps created during deformation of a sacrificial element such as the sacrificial element 150 will additionally signal that a sacrificial element is in need of repair or replacement and need not be filled.

Figure 5:
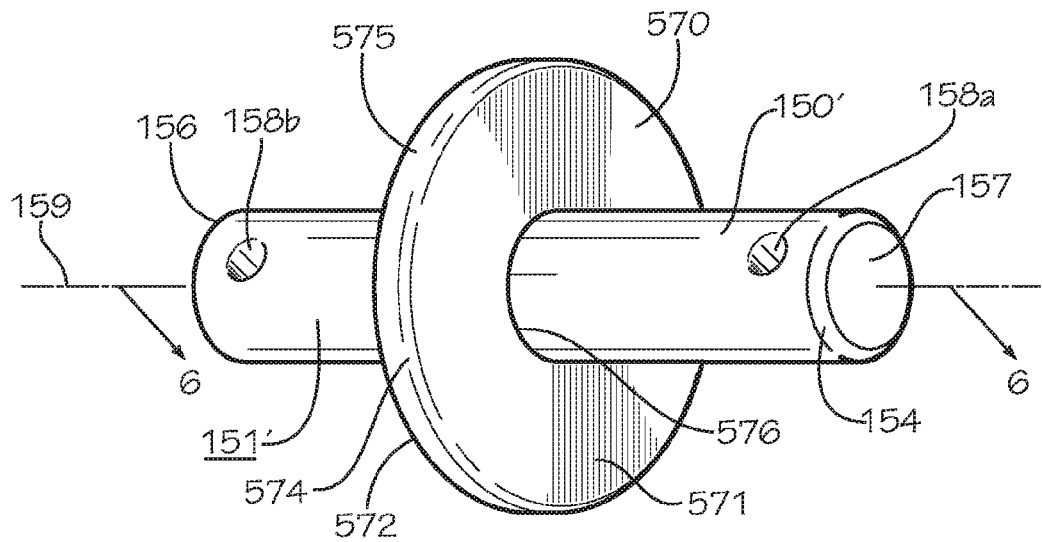
FIG. 5 is a perspective view of a sacrificial element of the sacrificial mechanical link of FIG. 1 in accordance with yet another aspect of the current disclosure.
Figure 6A:
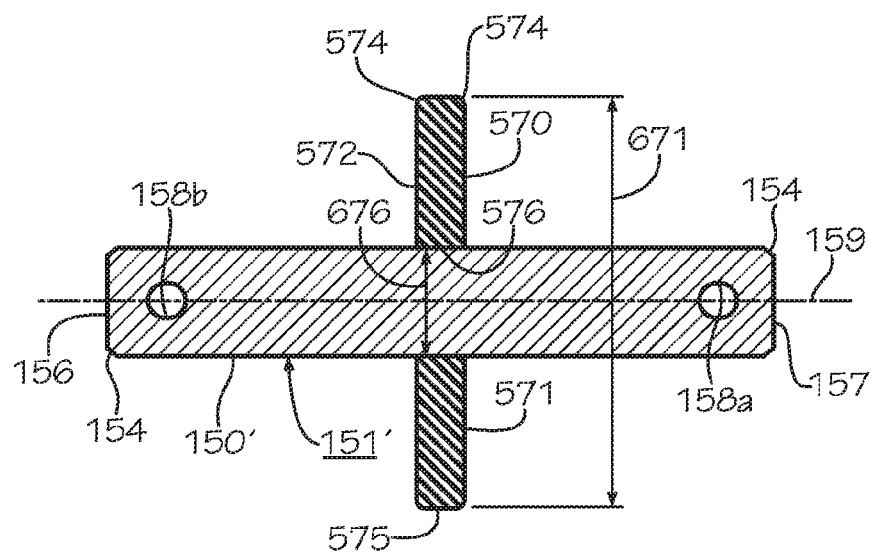
FIG. 6A is a sectional view of the sacrificial element of FIG. 5 taken along line 6-6 of FIG. 5.
Figure 6B:
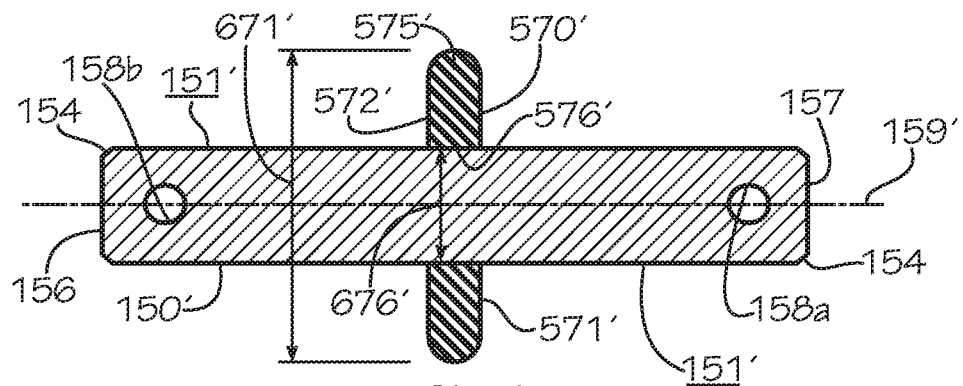
FIG. 6B is a sectional view of a sacrificial element of the sacrificial mechanical link of FIG. 1 in accordance with yet another aspect of the current disclosure.
Figure 6C:
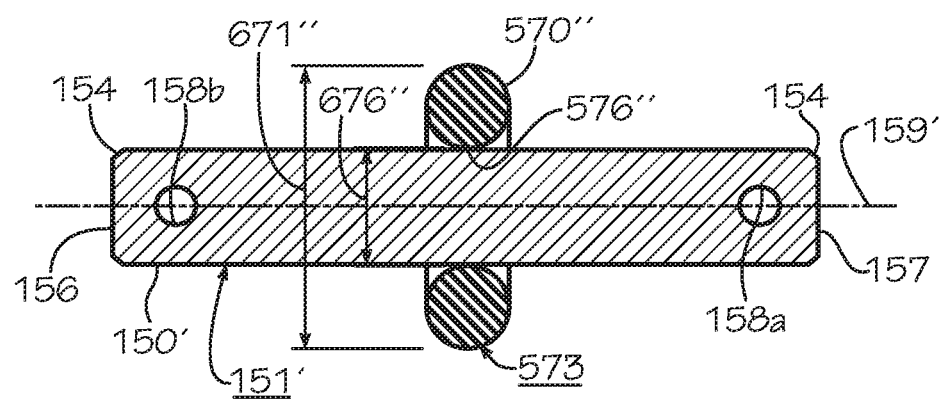
FIG. 6C is a sectional view of a sacrificial element of the sacrificial mechanical link of FIG. 1 in accordance with yet another aspect of the current disclosure.
Figure 6D:
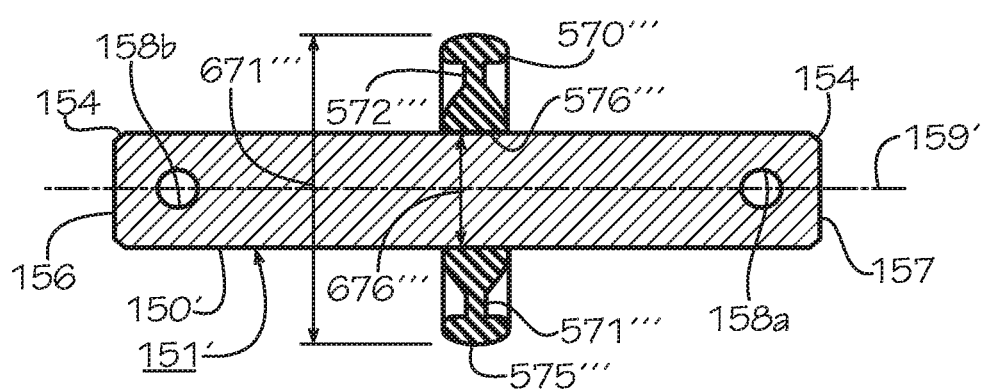
FIG. 6D is a sectional view of a sacrificial element of the sacrificial mechanical link of FIG. 1 in accordance with yet another aspect of the current disclosure.

Referring now to FIGS. 5-6D, in one aspect, a sacrificial element 150' can comprises the first end 156, the second end 157 and defines the attachment bore 158b and the attachment bore 158a proximate the first end 156 and the second end 157, respectively. In one aspect, and as shown in FIG. 6A, the sacrificial element 150' can also define the outer surface 151' and define the chamfered edges 154 at each of the first end 156 and the second end 157. In one aspect, a filler 570 can have a ring or a toroid shape, however, other conventional geometric shapes are contemplated. In one aspect, the filler 570 can comprise a first side 571, a second side 572, and a radially outer edge 575 and define a radiused edge 574 at each of the intersection of the first side 571 and the radially outer edge 575 and the intersection of the second side 572 and the radially outer edge 575. In this aspect, the filler 570 can define a bore 576 that can be sized to receive the sacrificial element 150' such that the sacrificial element 150' and the filler 570 are aligned along the same axis 159 of the sacrificial element 150'.

Optionally, the bore 576 of the filler 570 can have an inner diameter 676 that is substantially equal to or greater than an outer diameter of the sacrificial element 150'. In one aspect, the filler 570 can be separated from the sacrificial element 150' and can, for example and without limitation, be held in place by the first mechanical element 110 or the second mechanical element 120 or by both the first mechanical element 110 and the second mechanical element 120.

In another aspect, the filler 570 has the inner diameter 676 and an outer diameter 671. In this aspect, the outer diameter 671 can be sized so that the filler 570 extends beyond a radially outermost surface of the first mechanical element 110 or the second mechanical element 120 or beyond both the first mechanical element 110 and the second mechanical element 120. In this aspect, the bore 576 of the filler 570 can be positioned in contact with the outer surface 151' of the sacrificial element 150'.

In another aspect, and as shown in FIG. 6B, the sacrificial element 150' can comprise a filler 570' formed as shown. In this aspect, the filler 570' can have the shape of a toroid formed about the axis 159' and can comprise a first side 571', a second side 572', and a radially outer edge 575' and can define a bore 576' that is sized and shaped to receive the sacrificial element 150' such that both the sacrificial element 150' and the filler 570' are aligned along the axis 159'. In one aspect, the bore 576' can measure an inner diameter 676' that is substantially equal to or is greater than an outer diameter of the sacrificial element 150'. In this aspect, the filler 570' can be separated from the sacrificial element 150' and can be held in place by the respective first and second mechanical elements 110, 120. In this aspect, the filler 570' defines an outer diameter 671'.

In another aspect, and as shown in FIG. 6C, the sacrificial element 150' can comprise a filler 570" formed as shown. In this aspect, the filler 570" has the shape of a toroid formed about the axis 559'. In this aspect, the filler 570" can define an outer surface 573 and a bore 576" that is sized and shaped to receive the sacrificial element 150' such that both the sacrificial element 150' and the filler 570" are aligned along the axis 159'. In this aspect, the bore 576" can measure an inner diameter 676" that is substantially equal to or greater than an outer diameter of the sacrificial element 150'. In this aspect, the filler 570" can be separated from the sacrificial element 150' and can be held in place by the respective first and second mechanical elements 110,120. In this aspect, the filler 570" defines an outer diameter 671".

In another aspect, and as shown in FIG. 6D, the sacrificial element 150' can comprise a filler 570'". In this aspect, the filler 570'" has the shape of a toroid formed about the axis 159' and can comprise a first side 571'", a second side 572'", and a radially outer edge 575'". The filler 570'" can optionally define a bore 576'" that is sized and shaped to receive the sacrificial element 150' such that both the sacrificial element 150' and the filler 570'" are aligned along the axis 159'. In this aspect, the first side 571'" and the second side 572'" each define a surface that is shaped to match a corresponding cross-sectional shape of the end surfaces 201,202 of the respective first and second mechanical element 110,120. In this aspect, the bore 576'" can measure an inner diameter 676'" that is substantially equal to or greater than an outer diameter of the sacrificial element 150'. In this aspect, the filler 570'" can be separated from the sacrificial element 150' and can be held in place by the respective first and second mechanical elements 110,120. In this aspect, the filler 570''' can define an outer diameter 671'''. In this aspect, the outer diameter 671''' can be sized so that the filler 570''' extends beyond a radially outermost surface of the first mechanical element 110 or the second mechanical element 120 or beyond both the respective first and second mechanical elements 110,120.

Figure 7A:
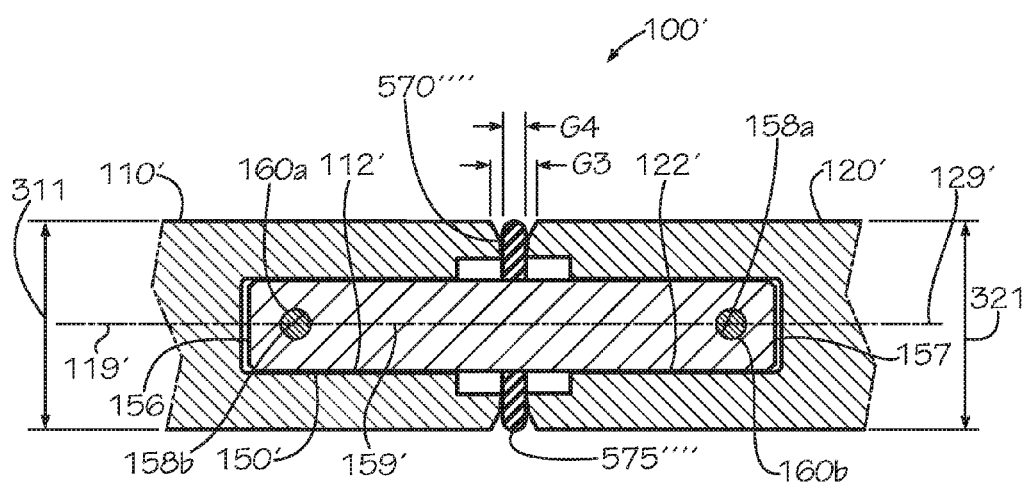
FIG. 7A is a detail sectional view of a sacrificial mechanical link taken in the same orientation as along lines 3-3 of FIG. 2 in accordance with yet another aspect of the current disclosure.
Figure 7B:
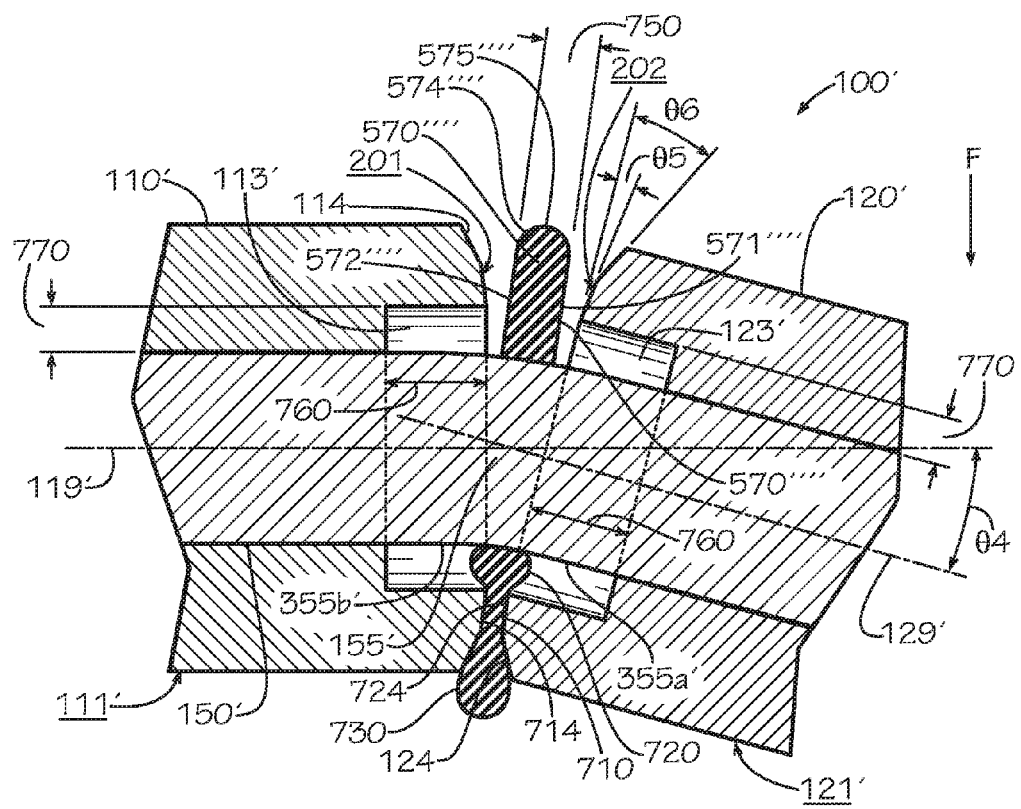
FIG. 7B is a detail sectional view of the sacrificial mechanical link of FIG. 7A in a deformed state.

In another aspect, and as shown in FIGS. 7A and 7B, a sacrificial mechanical link 100' comprising the sacrificial element 150' and a filler 570'''' is shown respectively in a non-deformed, assembled state and a deformed assembled state. In this aspect, the filler 570'''', can define radiused edges 574'''' on the outer edge 575'''' and can have an outer diameter equal to the matching outer diameters 311,321 of the respective first and second mechanical elements 110', 120'. In operation, when the connecting fastener 160a is installed in the attachment bores 118,158b and the connecting fastener 160b is installed in the attachment bores 128a, 158a, the end surface 201 of the first mechanical element 110 and the end surface 202 of the second mechanical element 120 can define a gap distance G3 and a gap distance G4 as shown. In an optional aspect, it is contemplated that the gap distance G3 can be larger than the gap distance G4 or the gap distance G3 can be substantially equal to the gap distance G4. As shown, the axis 159' can be aligned with the axis 119' of the first mechanical element 110' and with the axis 129' of the second mechanical element 120'.

In operation, when a force with at least a component force F is applied to the second mechanical element 120', the sacrificial element 150' can experience internal stresses beyond its elastic limit and can cause the sacrificial element 150' to deform where it is unsupported in the central portion 155'. One skilled in the art will appreciate that, while FIG. 7B shows the sacrificial element 150' as being deformed in a particular direction, the sacrificial element 150' is deformable in any horizontal direction between zero and 360 degrees, inclusive, when the axis 159 of the sacrificial element 150' is oriented along a substantially vertical axis.

In another aspect, it is contemplated that the sacrificial element 150', at least in part, can be made from a different material than that of the first mechanical element 110' or the second mechanical element 120'. In this aspect, a yield strength of a material forming the sacrificial element 150' can be lower than a yield strength of a material forming the first mechanical element 110' or a yield strength of a material forming the second mechanical element 120'. In optional aspects, the yield strength of a material forming the sacrificial element 150' can be equal to or greater than a yield strength of a material forming the first mechanical element 110' or a yield strength of a material forming the second mechanical element 120'. In these exemplary aspects, the sacrificial element 150' can still be configured to deform without deformation of the first mechanical element 110' or the second mechanical element 120' by sizing the first mechanical element 110' and the second mechanical element 120' such that the forces encountered by each result in lower internal stresses than encountered in the sacrificial element 150'.

Referring to FIG. 7B, a sufficiently high applied force F can cause the chamfered edge 114 of the first mechanical element 110' to approach the chamfered edge 124 of the second mechanical element 120' on a side opposite the side on which the force F is acting and thereby squeeze and deform the filler 570''''. In this aspect, each of the chamfered edges 114,124 of the respective end surfaces 201,202 can function as a stop to prevent further movement (i.e., bending) of the first mechanical element 110' with respect to the second mechanical element 120'. In this aspect, the axis 119' of the first mechanical element 110' and the axis 129' of the second mechanical element 120' define a maximum deformation angle θ4 between the axes 119',129'. In this aspect, it is contemplated that the maximum deformation angle θ4 can be at least 1°, at least 2°, at least 3°, at least 4°, or at least 5°. Optionally, the maximum deformation angle can be between about 0.5° to about 25°, or between about 1° to about 15°.

In one aspect, the definition of an end cavity 113' in the first mechanical element 110' and the definition of an end cavity 123' in the second mechanical element 120' facilitate deformation of the sacrificial element 150' by providing a space for the central portion 155' of the sacrificial element 150' and for the filler 570'''' to freely deform. In one aspect when the filler 570'''' is deformed, a pinched portion 710 is compressed to a fraction of its original thickness equal to a thickness 750 of the filler 570''''; an inwardly deformed portion 720 is squeezed into the space defined between and including the end cavity 113' and the end cavity 123' and radially inward from the end surfaces 201,202; and an outwardly deformed portion 730 is squeezed out of the gap previously defined by gaps G3,G4 and radially outward from the outer surfaces 111',121' of the respective first and second mechanical elements 110',120'. In one aspect, the shape of the end surfaces 201,202 can facilitate compression of the filler 570'''' by concentrating the pinching force resulting from the force F onto a smaller area of the first side 571'''' and second side 572'''' of the filler 570''''. In one aspect, the applied force F can result in a pinching force sufficient to partially or completely shear through a filler such as the filler 570''''. In one aspect, the end surface 202 defines a first chamfer angle θ5 between a first chamfered edge 724 and relative to a cross-sectional plane extending perpendicular to the axis 129' of the second mechanical element 120' and a second chamfer angle θ6 between a second chamfered edge and relative to a cross-sectional plane extending perpendicular to the axis 129' of the second mechanical element 120'. In a similar aspect, the end surface 201 can define a chamfer angle between a first chamfered edge 714 and a plane perpendicular to the axis 119' of the first mechanical element 110' and a chamfer angle between a second chamfered edge represented by the chamfered edge 114 and the same plane perpendicular to the axis 119' of the first mechanical element 110'.

In one aspect, the shape of the respective end cavities 113', 123' can be configured to reduce or eliminate localized stresses where the sacrificial element 150' enters the main bore 112' of the first mechanical element 110' or the main bore 122' of the second mechanical element 120'. In one aspect, the sacrificial mechanical link 100', the first mechanical element 110' and the second mechanical element 120' can define the end cavities 113',123' at an entrance to the main bores 112',122'. In one exemplary aspect, and not meant to be limiting, the end cavities 113',123' can be annular in shape overall and/or rectangularly shaped in cross-section. In this aspect, an axial dimension 760 of each of the end cavities 113',123' can be greater than a radial dimension 770 of the respective end cavities 113',123'.

In one aspect, the common sacrificial element 150' can be used in multiple joints and the size and shape of the end surfaces 201 in the first mechanical element 110' and the end surfaces 202 in the second mechanical element 120', to exemplarily include the size and shape of the end cavities 113',123' and/or the gap distances G3,G4, can be selectively adjusted to achieve similar deformation as with a sacrificial element 150' made from a different material or having a different size or shape. In one aspect, by decreasing the size of the gap distances G3,G4 or by reducing the axial dimension 760 of the end cavities 113',123' from a first sacrificial mechanical link 100' to a second mechanical link 100', additional surface area of the outer surface 151' of the sacrificial element 150', and specifically in the central portion 155', can be additional supported and the sacrificial element 150' can be restrained in such a way as to prevent deformation that would otherwise occur under a given force. As exemplarily illustrated in FIG. 7B, a portion 355b' of the outer surface 151' of the sacrificial element 150' can be left unsupported by the first mechanical element 110' due to the inclusion of the end cavity 113', and a portion 355a' of the outer surface 151' of the sacrificial element 150' can be left unsupported by the second mechanical element 120' due to the inclusion of the end cavity 123'.

Figure 8:
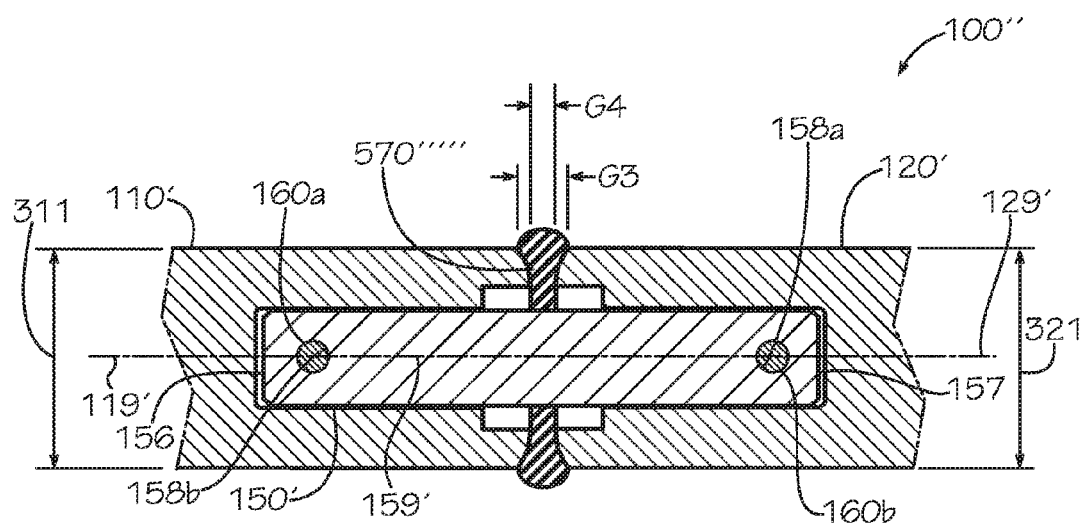
FIG. 8 is a detail sectional view of a sacrificial mechanical link taken in the same orientation as along lines 3-3 of FIG. 2 in accordance with yet another aspect of the current disclosure.

Referring now to FIG. 8, in one aspect, a sacrificial mechanical link 100" comprising the sacrificial element 150' and a filler 570"" is shown in a non-deformed, assembled state. In this aspect, except for the size and shape of the filler 570"", it is contemplated that the construction of the sacrificial mechanical link 100" is similar to that of the sacrificial mechanical link 100'. In this aspect, the filler 570"", while similar to the other fillers 570 and particularly the filler 570"" disclosed herein, defines an outer edge 575"" having an outer diameter greater than the matching outer diameters 311, 321 of the respective first and second mechanical elements 110', 120' and can be flared and rounded to fill gap distances G3,G4. The axis 159' of the sacrificial element 150' is shown aligned with the axis 119' of the first mechanical element 110' and with the axis 129' of the second mechanical element 120'.

In one aspect, the filler 570"" can be configured to fill a gap between the first mechanical element 110' and the second mechanical element 120' and to extend to the respective outer surfaces 111', 121' when the sacrificial mechanical link 100' is in a non-deformed state.

In one aspect, it is contemplated that filler 570 can made from any material that will compress under the loads experienced inside a sacrificial mechanical link such as the sacrificial mechanical link 100. In this aspect, it is contemplated that filler 570 can comprise one or more of a set of materials including, but not limited to, elastomers such as natural or synthetic rubbers (such as neoprene), plastics, and foam materials. In optional aspects, the material the filler 570 can have a low compressibility to resist compression or high compressibility to more easily compress. In one aspect, the filler 570 has a very low durometer relative to all of the other parts of the sacrificial mechanical link and is easily deformed and/or displaced when the sacrificial mechanical link is deformed. In another aspect, the material the filler 570 can be selected based on its ability to not only compress but to shear as needed so that a sacrificial element such as the sacrificial element 150 is free to deform and so that mechanical elements such as the mechanical elements 110,120 are free to bend with respect to one another to give a user the desired indication that overloading of a sacrificial mechanical link has occurred.

In a further aspect, a chemiluminescent or similar "glow-in-the-dark" material can be used in the filler. In one aspect, a filler can further comprise a chemiluminescent material that can be configured to give off light when the filler experiences a force sufficient to deform the shape of the filler 570. For example, when a thin wall between separate chambers within the filler 570"" containing separate subcomponents of the chemiluminescent material is breached by physical cracking of the wall, the subcomponents can mix, react, and in the process give off a light. In aspect, the time duration, color and intensity of the light can be selectively adjusted. In one aspect, a stronger color (red) or a more intense light can be used where the load required to trigger or overload the sacrificial mechanical link is higher or where the equipment being protected is a more critical piece of equipment. In this aspect, the light produced gives a clear and immediate indication to the user of the equipment including the sacrificial mechanical link 100' that overloading has occurred.

Figure 9:
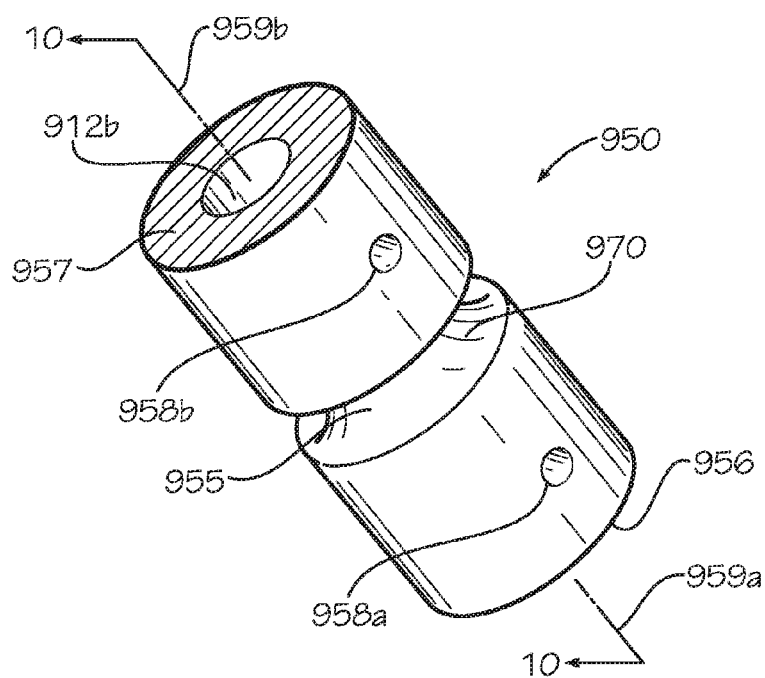
FIG. 9 is a perspective view of a sacrificial element in accordance with another aspect of the current disclosure.
Figure 10:
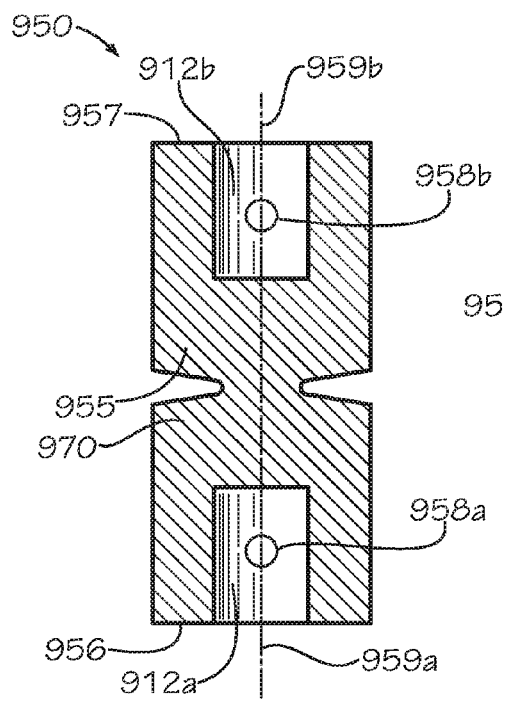
FIG. 10 is a sectional view of the sacrificial element of FIG. 9 taken along line 10-10 of FIG. 9.
Figure 11:
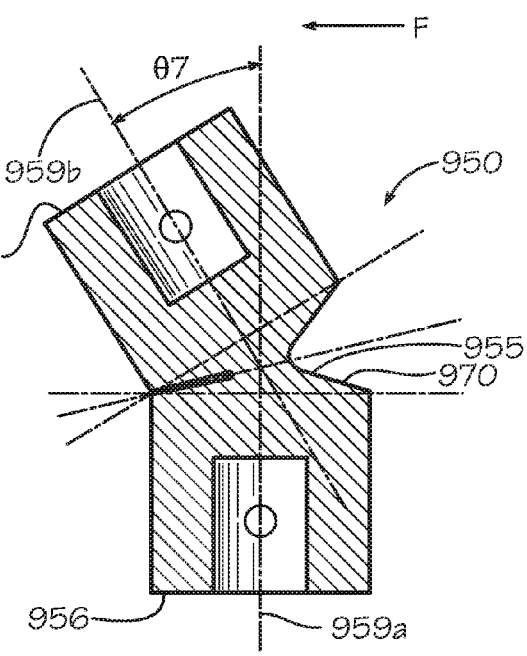
FIG. 11 is a sectional view of the sacrificial element of FIG. 9 in a deformed state.

Referring now to FIGS. 9-11, a sacrificial element 950 comprises a first end 956, a second end 957, and a central portion 955 is shown. In this aspect, the sacrificial element 950 can define inner bores 912a,b in the respective first and second ends 956, 967 that are configured to receive a first mechanical element and a second mechanical element. In this exemplary aspect, the sacrificial element 950 can defines attachment bores 958a,b for receiving connecting fasteners such as the connecting fasteners 160. In one aspect, the first end 956 of the sacrificial element 950 defines an axis 959b and the second end 957 of the sacrificial element 950 defines an axis 959a.

In one exemplary aspect, and not mean to be limiting, the central portion 955 of the sacrificial element that can define a parabolic shape in cross-section that is narrowest at a radially innermost portion and widest at a radially outermost portion. It is contemplated that the neck 970 can be any one of a number of geometric shapes wherein a diameter of the neck 970 is less than a diameter of the respective ends 956,957. In one aspect, the shape of the neck 970 of the sacrificial element 950 will limit bending of the axis 959b to a maximum deformation angle θ7 relative to the axis 959a. In one aspect, it is contemplated that the size, shape, and location of the neck 970 can be selectively adjusted to adjust the maximum deformation angle θ7.

In one aspect, in operation, the sacrificial element is configured to deform after a force F is applied to the second end 957 of the sacrificial element 950 that is sufficient to cause the axis 959b to bend with respect to the axis 959a by an angle substantially equal to the maximum deformation angle θ7. As noted above, it is contemplated that the respective upper and lower opposing surfaces of the neck 970 will contact each other to prevent further rotation of the sacrificial element 950 past the maximum deformation angle θ7. In one aspect, one skilled in the art will appreciate that the material of the sacrificial element in the central portion 955 in the area of the neck 970 can undergo a form of work hardening due to its being "cold worked" at room temperature such that further deformation of the sacrificial element 950 becomes progressively more difficult.

Referring now to FIG. 12, in one aspect, a sacrificial mechanical link 100 installed in a receiver arm 4652 of a mobile support platform 4650 of a transfer system is shown. In this exemplary aspect, the first mechanical element 110 can be selectively attached to a hospital bed frame or other mobile equipment. The second mechanical element 120 can be connected to the first mechanical element 110 with a sacrificial element 150 by installing the connecting fasteners 160a,b through a pair of respective attachment bores 118b, 128a. In one aspect, a receiver 4615 can be supported by an arm 4840 that is sized and shaped to receive a transfer device 4631. In one aspect, the receiver arm 4652 can be rigidly attached to the second mechanical element 120—using an attachment bore 128b receiving a connecting fastener not shown, for example—in such a way that the receiver arm 4652 will not bend with respect to the second mechanical element 120. In a non-deformed state, it is contemplated that an axis 1229 of the second mechanical element 120 is aligned with an axis 1219 of the first mechanical element 110. In one aspect, the sacrificial mechanical link 100' can replace the sacrificial mechanical link 100 in the mobile support platform 4650. For example, in operation, when the sacrificial mechanical link 100 is overloaded by an applied force applied to the receiver 4615, the receiver 4615 together with the coupled second mechanical element 120 tends to bend with respect to the first mechanical element 110 to form an angle (not shown) between the axis 1219 and the axis 1229.

Referring now to FIG. 13, in one aspect, a sacrificial mechanical link 1300 installed in a receiver arm 4652' of a mobile support platform 4650' is shown. In one aspect, the sacrificial mechanical link 1300 can comprise an adapter shaft 4710 functioning as a first mechanical element, a receiver arm 4652' functioning as a second mechanical element, a first connecting element 1350a, a second connecting element 1350b, and the sacrificial element 950. In this aspect, the first connecting element 1350a and the second connecting element 1350b are not intended to function as sacrificial elements but rather to connect the sacrificial element 950 to the adapter shaft 4710 and the receiver arm 4652', respectively. Thus, in one aspect, the first connecting element 1350a and the second connecting element 1350b can each made from a material and/or formed into a geometry that is able to withstand loads under which the sacrificial element 950 would deform. In this aspect, the first connecting element 1350a can connect the adapter shaft 4710 and the first end 956 of the sacrificial element 950 with a first pair of connecting fasteners 160a,b, respectively and the second connecting element 1350b can connect the receiver arm 4652' and the second end 957 of the sacrificial element 950 with a second pair of connecting fasteners 160c,d, respectively. In one aspect, a receiver 4615 is configured to be supported by an arm 4840' that it sized and shaped to receive a transfer device 4631. In a non-deformed state, an axis 1329 of the receiver arm 4652' is configured to be aligned with an axis 1319 of the adapter shaft 4710. For example, in operation, when the sacrificial mechanical link 1300 is overloaded by an applied force applied to the receiver 4615, the receiver 4615 tends to bend together with the arm 4840' and the second end 957 of the sacrificial element 950 to form an angle (not shown) between the axis 1319 and the axis 1329.

Referring now to FIG. 14, in one aspect, a sacrificial element 1450 comprises a first end 1456, a second end 1457, and a central portion 1455. In one exemplary aspect, and not meant to be limiting, the sacrificial element 1450 can be circular in cross-section at the first end 1456 and at the second end 1457 but can be rectangular in cross-section at a neck 1470 of the central portion 1455. In this aspect, the sacrificial element 1450 defines inner bores 1412a,b in the respective first and second ends 1456,1457 for receiving a first mechanical element and a second mechanical element. In one aspect, the sacrificial element 1450 can define attachment bores 1458a,b that are configured for receiving connecting fasteners such as the connecting fasteners 160. In this aspect, the first end 1456 of the sacrificial element 1450 can define an axis 1459b and the second end 1457 of the sacrificial element 1450 can define an axis 1459a. In one aspect, the neck 1470 can define a first bending axis 1401 and a second bending axis 1402. In this aspect, the neck is configured such that the minimal moment of inertia is about the respective first and second bending axes 1401,1402.

Referring now to FIG. 15, in one aspect, a sacrificial element 1550 comprises a first end 1556, a second end 1557, and a central portion 1555 is shown. In one exemplary aspect, and not meant to be limiting, the sacrificial element 1550 can be square in cross-section at the first end 1556 and at the second end 1557 but can be formed to be circular in cross-section at a neck 1570 of the central portion 1555. In this aspect, a first mechanical element and a second mechanical element can be sized to receive the respective first and second ends 1556,1557 of the sacrificial element 1550. In this aspect, the sacrificial element 1550 can define inner bores in the respective first and second ends 1556,1557 for receiving a first mechanical element and a second mechanical element. In this aspect, the sacrificial element 1550 can defines attachment bores 1558a,b for receiving connecting fasteners such as the connecting fasteners 160. In one aspect, the first end 1556 of the sacrificial element 1550 defines an axis 1559b and the second end 1557 of the sacrificial element 1550 defines an axis 1559a.

Referring now to FIG. 16, in one aspect, a sacrificial element 1650 comprises a first end 1656, a second end 1657, and a central portion 1655 as shown. In one exemplary aspect, and not meant to be limiting, the sacrificial element 1650 can be circular in cross-section at the first end 1656 and at the second end 1657 but can be formed to be substantially square or rectangular in cross-section at a first neck 1670a and at a second neck 1670b of the central portion 1655. In this aspect, but not meant to be limiting, it is contemplated that the size and shape of the first neck 1670a can be substantially similar to the size and shape of the first neck 1670a. In one aspect, a bending axis 1602 defined by the second neck 1670b can be oriented in a horizontal plane at 90° relative to a bending axis 1602 defined by the first neck 1670a. In this aspect, the sacrificial element 1650 can define inner bores 1612a,b in the respective first and second ends 1656,1657 for receiving a first mechanical element and a second mechanical element. In one aspect, the sacrificial element 1650 can define attachment bores 1658a,b for receiving connecting fasteners such as the connecting fasteners 160. In this aspect, the first end 1656 of the sacrificial element 1650 can define an axis 1659b and the second end 1657 of the sacrificial element 1650 can define an axis 1659a. In one aspect, the second end 1657 is configured to bend with respect to the first end 1656 about the respective bending axes 1601,1602, which are configured to have the lowest moment of inertia of the sacrificial element.

FIG. 17A discloses and describes another aspect of a sacrificial mechanical link in the form of a sacrificial mechanical link 1700 in a non-deformed state. The sacrificial mechanical link 1700 comprises the first mechanical element 1710 resembling a shaft, the second mechanical element 1720 resembling a pole, and a sacrificial element 1750 resembling an offset arm. In one aspect, the first mechanical element 1710 comprises a first end 1716 and a second end 1717. In one aspect, the second mechanical element 1720 comprises a first end 1726 and a second end (not shown) distal the first end 1726. In one aspect, the sacrificial element 1750 comprises a first end 1756, a second end 1757, and a center portion 1755 including a neck portion 1770. In one aspect, the neck portion 1770 defines a first sloped surface 1771, a second sloped surface 1772 at least partly facing the first sloped surface 1771, and a relief 1780 that is cylindrically shaped at its deepest point. In one aspect, an angle θ8 between the first sloped surface 1771 and the second sloped surface 1772 is greater than zero degrees but less than 180 degrees. The second sloped surface 1772 is configured to approach the first sloped surface 1771 between a non-deformed state of the sacrificial mechanical link 1700 and a deformed state of the sacrificial mechanical link 1700. Optionally, the sacrificial mechanical link includes a filler 1870 that has similar properties and a similar purpose as the aforementioned filler 570. In various other aspects, the angle θ8 is zero degrees or the first sloped surface 1771 and the second sloped surface 1772 slope in an opposite direction from that shown (i.e., towards each other). In one aspect, bringing the mating surfaces or edges of the first sloped surface 1771 and the second sloped surface 1772 closer together provides a smaller maximum deformation angle θ9 (shown in FIG. 17B) when the sacrificial mechanical link 1700 is overloaded than is possible with the first sloped surface 1771 and the second sloped surface 1772 sloped as shown. In one aspect, however, the maximum deformation angle θ9 does not match the angle θ8.

In one aspect, the sacrificial element 1750 defines a first bore 1712a and a second bore 1712b for receiving the first mechanical element 1710 and the second mechanical element 1720, respectively. In one aspect, the second end 1717 of the first mechanical element 1710 is connected to the sacrificial element 1750 with a connecting fastener 1760a installed in an attachment bore 1758a in the sacrificial element 1750 and in an attachment bore (not shown) in the first mechanical element 1710. In one aspect, the first end 1726 of the second mechanical element 1720 is connected to the sacrificial element 1750 with a connecting fastener 1760b installed in an attachment bore 1758a in the sacrificial element 1750 and in an attachment bore (not shown) in the second mechanical element 1720.

When loading of the sacrificial mechanical link 1700 occurs sufficient to cause the intended deformation of the sacrificial element 1750, this deformation occurs about a bend line 1791 shown because the cross-section of the sacrificial element 1750 at the bend line 1791 has a smaller moment of inertia than at any other sections of the sacrificial element 1750 carrying or experiencing a bending load in actual use. In one aspect, the first mechanical element 1710 defines an axis 1719 and the second mechanical element 1720 defines an axis 1729 that is parallel in one aspect to the axis 1719 when the sacrificial mechanical link 1700 is in a non-deformed state. When the sacrificial mechanical link 1700 is overloaded, the second mechanical element 1720 tends to bend with respect to the first mechanical element 1710 such that the maximum deformation angle θ9 forms between the two portions of the sacrificial element 1750 bent with respect with one another as shown in FIG. 17B (which angle matches an angle formed between the axis 1719 and the axis 1729.

Figure 18:
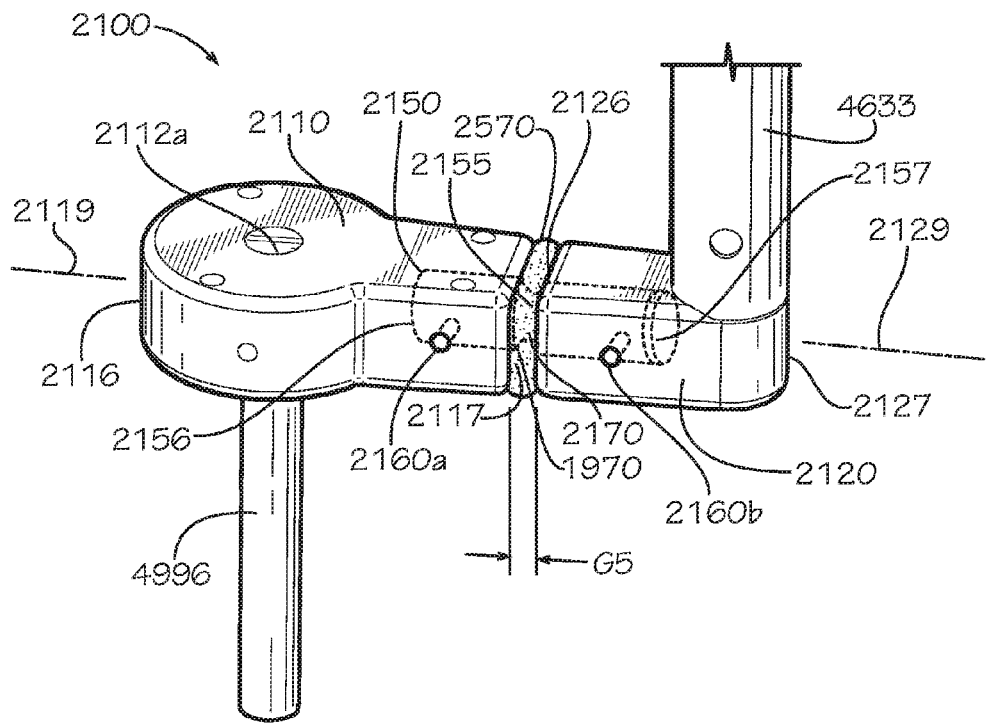
FIG. 18 is a perspective view of a sacrificial mechanical link in accordance with yet another aspect of the current disclosure.
Figure 19:
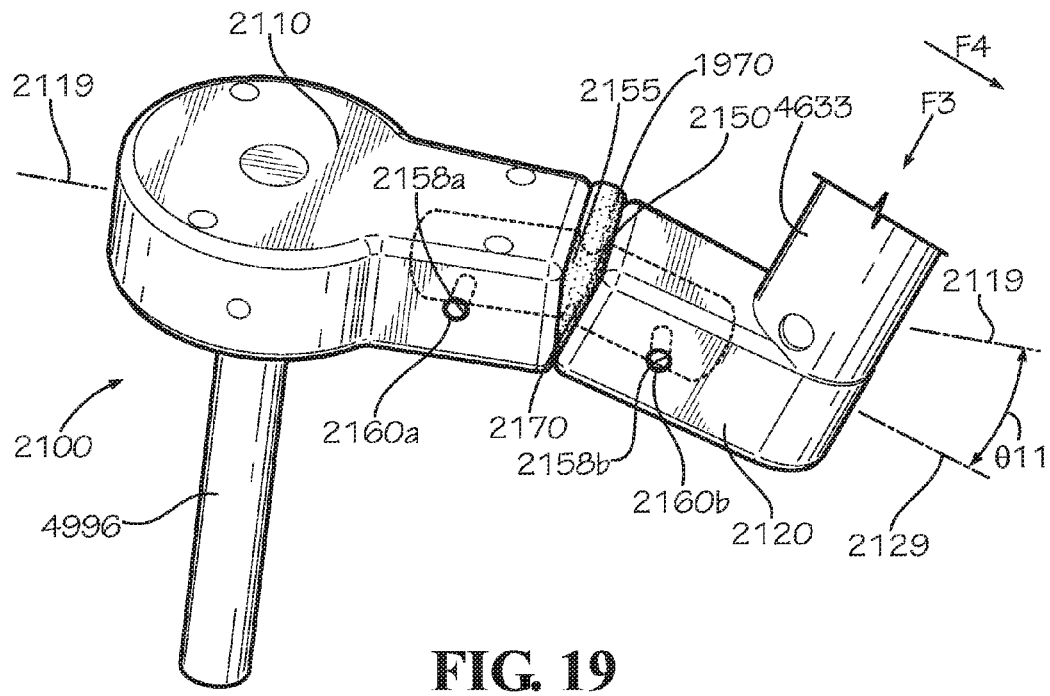
FIG. 19 is a perspective view of the sacrificial mechanical link of FIG. 18 in a deformed state.

FIGS. 18 and 19 disclose and describe another aspect of a sacrificial mechanical link in the form of a sacrificial mechanical link 2100. The sacrificial mechanical link 2100 comprises a first mechanical element 2110 resembling a first portion of an offset arm of a transfer apparatus, a second mechanical element 2120 resembling a second portion of an offset arm of a transfer apparatus, and a sacrificial element 2150 resembling a deformable rod connecting the first mechanical element 2110 and the second mechanical element 2120. In one aspect, the first mechanical element 2110 comprises a first end 2116 and a second end 2117. In one aspect, the second mechanical element 2120 comprises a first end 2126 and a second end 2127. In one aspect, the sacrificial element 2150 comprises a first end 2156, a second end 2157, and a center portion 2155 including a neck portion 2170 and a filler 1970. In one aspect, the neck portion 2170 has a concave side cross-section. In one aspect, the neck portion 2170 decreases in diameter towards the center of a gap distance G5 defined between the second end 2117 of the first mechanical element and the first end 2126 of the second mechanical element 2120 when the sacrificial mechanical link 2100 is in a non-deformed state. In one aspect, the gap distance G5 at least partly determines a maximum deformation angle θ11 (shown in FIG. 19) of the sacrificial mechanical link 2100. In one aspect, bringing the mating surfaces or edges of the second end 2117 of the first mechanical element 2110 and the first end 2126 of the second mechanical element 2120 closer together provides a smaller maximum deformation angle when the sacrificial mechanical link 2100 is overloaded than is possible with the sacrificial mechanical link 2100 as shown.

In one aspect, the first mechanical element 2110 defines a first bore 2112a for receiving a support shaft 4996 and the second mechanical element 2120 defines a second bore (not shown) for receiving a support pole 4633. In one aspect, the second end 2117 of the first mechanical element 2110 is connected to the sacrificial element 2150 with a connecting fastener 2160a installed in an attachment bore 2118a of the first mechanical element 2110 and in an attachment bore (not shown) of the sacrificial element 2150. In one aspect, the first end 2126 of the second mechanical element 2120 is connected to the sacrificial element 2150 with a connecting fastener 2160b installed in an attachment bore 2158b of the second mechanical element 2120 and in an attachment bore (not shown) of the sacrificial element 2150.

When loading of the sacrificial mechanical link 2100 occurs sufficient to cause the intended deformation of the sacrificial element 2150, this deformation occurs in the neck portion 2170 of the sacrificial element 2150 because the neck portion 2170 has a smaller moment of inertia than any other section of the sacrificial element 2150, the first mechanical element 2110, or the second mechanical element 2120 carrying a bending load in actual use. In one aspect, the first mechanical element 2110 defines an axis 2119 and the second mechanical element 2120 defines an axis 2129 that is aligned with the axis 2119 when the sacrificial mechanical link 2100 is in a non-deformed state. When the sacrificial mechanical link 2100 is overloaded by a force F3 or a force F4 as shown in FIG. 19, the second mechanical element 2120 tends to bend with respect to the first mechanical element 2110 to form the maximum deformation angle θ11 between the axis 2119 and the axis 2129. The filler 1970 is formed from such a material (such as that described with respect to the filler 570) that it can fill the gap distance G5 when the sacrificial mechanical link 2100 is in a non-deformed state and yet deform or become displaced when the sacrificial mechanical link 2100 is in a deformed state.

Figure 20:
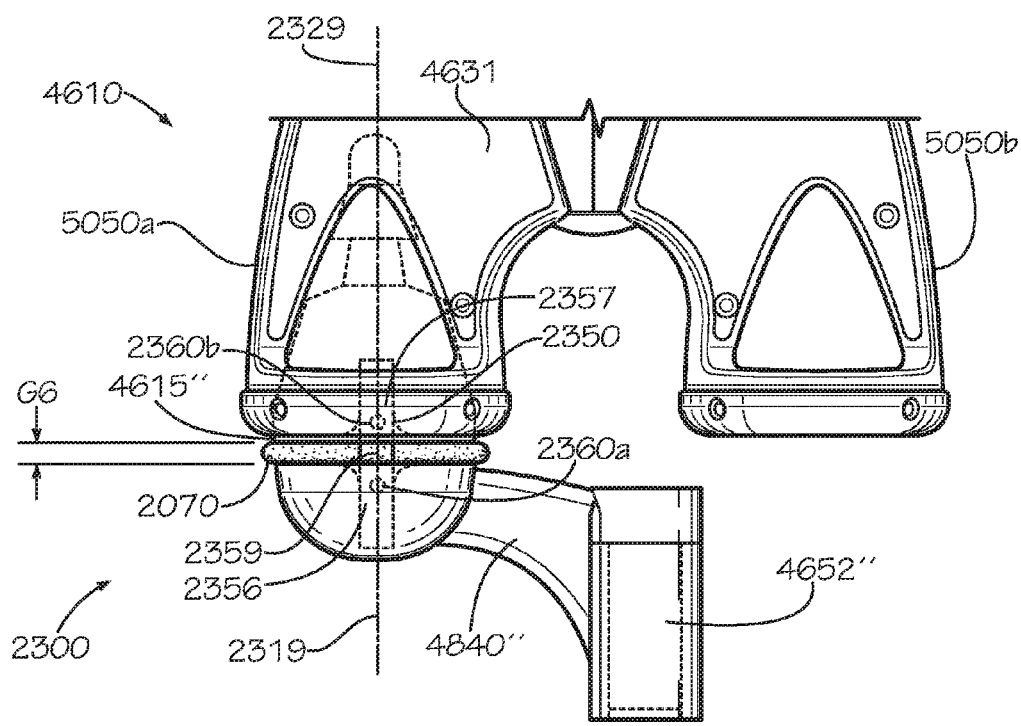
FIG. 20 is a side view of a sacrificial mechanical link installed in a receiver arm of a transfer system in accordance with one aspect of the current disclosure.

FIG. 20 discloses and describes another aspect of a sacrificial mechanical link installed in a portion of a stationary support platform 4610 (mounting structure not shown) in the form of a sacrificial mechanical link 2300. In one aspect, the stationary support platform 4610 comprises a receiver arm 4652", the receiver arm 4652" including a receiver 4615" and an arm 4840". In one aspect, the sacrificial mechanical link 2300 comprises the arm 4840" functioning as a first mechanical element, the receiver 4615" functioning as a second mechanical element, and a sacrificial element 2350. In one aspect, a first end 2356 of the sacrificial element 2350 is connected to the arm 4840" by a connecting fastener 2360a, and a second end 2357 of the sacrificial element 2350 is connected to the receiver 4615" by a connecting fastener 2360b. In one aspect, the connecting element 2390 is not intended to function as a sacrificial element but rather to connect the receiver arm 4652" to the connecting link arm 4613. Thus in one aspect, the first connecting element 2390 is made from a material and formed into a geometry that is able to withstand loads under which the sacrificial element 2350 would deform. In one aspect, the receiver 4615" is sized to receive one of a docking cup 5050a and a docking cup 5050b of a transfer device 4631. In a non-deformed state, an axis 2329 of the receiver 4615" is aligned with an axis 2319 of the arm 4840", and both the axis 2329 and the axis 2319 are aligned with an axis 2359 of the sacrificial element 2350. When the sacrificial mechanical link 2300 is overloaded by a force (not shown) such as when a force is applied to the transfer device 4631 when the transfer device 4631 is connected to the receiver 4615", the receiver 4615" tends to bend with respect to the arm 4840" to form an angle (not shown) between the axis 2319 and the axis 2329.

In one aspect, the receiver 4615" is spaced away from the arm 4840" by a gap distance G6 when the sacrificial mechanical link 2300 is in a non-deformed state. Optionally, the gap described by the gap distance G6 can be filled with a filler 2070 as shown that, like the filler 570, eliminates any pinch points in the sacrificial mechanical link 2300. In one aspect, the gap distance G6 allows for the receiver 4615" to bend with respect to the arm 4840" to an angle (not shown) between the axis 2319 and the axis 2329 sufficient to provide notice to a user that the sacrificial mechanical link 2300 has been overloaded and requires inspection and repair.

In one aspect, at least in part because the center line of a patient support apparatus such as an IV pole does not always align with the centerline of a receiver such as the receiver 4615", locating a "fuse" element such as the sacrificial element 2350 to lie concentric with the axis of the receiver 4615" minimizes the difference of load cantilevers regardless of the orientation—including the angular orientation in a horizontal plane—of the transfer device 4631.

FIGS. 21-23 disclose another aspect of the stationary support platform 4610 comprising the receiver arm 4652", the receiver arm 4652" again including the receiver 4615" and the arm 4840".

The sacrificial element 2350 is shown slightly longer in FIGS. 21-23 than in FIG. 20 and additionally with a neck 2370 at a central portion 2355. In one aspect, the shape and diameter of the neck 2370 can be sized for the desired degree of bendability in consideration of the ductility of the material used to form the sacrificial element 2350. While the first end 2356 of the sacrificial element 2350 is shown symmetric with respect to the second end 2357, the first end 2356 of the sacrificial element 2350 can be made asymmetric (i.e., longer or shorter) with respect to the second end 2357. In one aspect, the connecting fastener 2360a extends through and secures inside an attachment bore 2358a and the connecting fastener 2360b extends through and secures inside an attachment bore 2358b. FIG. 21 shows the axis 2329 of the receiver 4615" aligned with the axis 2319 of the arm 4840", and both the axis 2329 and the axis 2319 are aligned with an axis 2359 of the sacrificial element 2350. When the sacrificial mechanical link 2300 is overloaded by a force (not shown), the receiver 4615" tends to bend with respect to the arm 4840" to form a maximum deformation angle θ12 between the axis 2319 and the axis 2329. In one aspect, the gap distance G6 allows the receiver 4615" to bend in any direction. In one aspect, the sacrificial mechanical link 2300 comprises a filler 2270. In one aspect, the filler 2270 fills the gap described by the gap distance G6 and provides various benefits including, but not limited to, the elimination of pinch points, improved infection control, and some of the other benefits previously mentioned with respect to a filler or gasket such as the filler 570.

Figure 24:
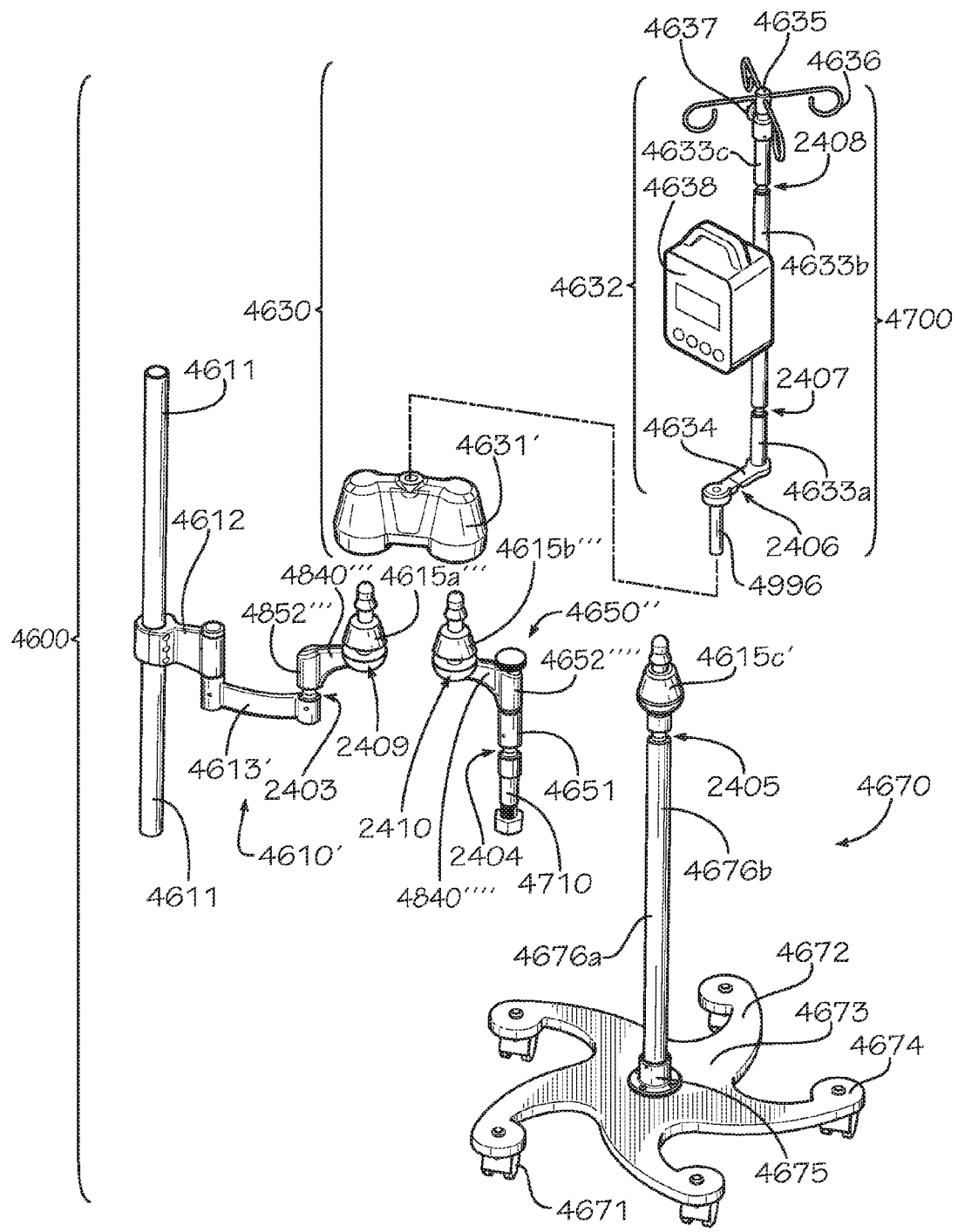
FIG. 24 is a transfer system including a sacrificial mechanical link in each of a variety of locations of the transfer system according to one aspect of the current disclosure.

FIG. 24 discloses a transfer system 4600 including sacrificial mechanical links 2403-2410 in each of a variety of representative locations. Each of the sacrificial mechanical links 2403-2410 can be any one of the disclosed aspects of a sacrificial mechanical link including the sacrificial mechanical links 100, 100', 100", 1300, 1800, 2000, 2100, 2300; or can include any one of the sacrificial elements 50, 150', 950,1450, 1550, 1650, 1700, 1700', 1850, 2050, 2150, 2350. In one aspect, each of the sacrificial mechanical links 2403-2410 can include a variation or combination or any one or more of the aspects or features disclosed herein.

The transfer system 4600 include a transfer apparatus 4630, a stationary support platform 4610', a mobile support platform 4650", and a mobile stand-alone support platform 4670. The disclosed elements of the transfer system 4600 are simply exemplary of a type of transfer system with which other elements not shown would be compatible and could include. In one aspect, only one sacrificial mechanical link is installed in a transfer system such as the transfer system 4600. In one aspect, only one sacrificial mechanical link is installed in each discrete subsystem of a transfer system such as the transfer system 4600 including, but not limited to, the transfer apparatus 4630, the stationary support platform 4610', the mobile support platform 4650", and the mobile stand-alone support platform 4670. For example, in a portion of a transfer system including only the transfer apparatus 4630 and the mobile support platform 4650" attached to a hospital bed, a single sacrificial mechanical link in the form of the sacrificial mechanical link 2410 can be installed in the mobile support platform 4650". In one aspect in use where the transfer apparatus 4630 comes into contact with a stationary object during transport of the hospital bed through a hospital and that contact is sufficient to cause overloading of a sacrificial mechanical link in the system, overloading and activation of only the sacrificial mechanical link 2410 is sufficient to protect not only the hospital bed but also the individual components of the transfer apparatus 4630 that can otherwise be damaged by a rigidly connected system with no sacrificial mechanical link.

The transfer apparatus 4630 of FIG. 24 comprises a transfer device 4631' and a patient care apparatus 4632. The patient care apparatus 4632 comprises an offset arm 4634 and a pole—shown as three pole segments 4633a,b,c—that is an IV pole in the current aspect. The patient care apparatus 4632 also comprises a patient care device 4638—shown as an IV pump in the current aspect. As will be explained in further detail, a center of gravity of the patient care device 4638 is located directly over the support shaft 4996 in one aspect of the patient care apparatus 4632. In one aspect, the patient care apparatus 4632 comprises multiple IV poles, one or more IV infusion pumps, or another type of patient care device mountable either directly or indirectly on the pole 4633 or the offset arm 4634 or another portion of the patient care apparatus 4632. In one aspect, the patient care apparatus 4632 comprises a top portion 4635 and an adjustment knob 4637 to allow the top portion 4635 to be raised or lowered with respect to the pole represented by the pole segments 4633. In one aspect, the top portion 4635 comprises hooks 4636. In one aspect, hooks 4636 can take on any number of different shapes and are not limited to the "rams-horn" style shown. In one aspect, the quantity of hooks 4636 varies from that shown. In one aspect, a patient care support structure 4700 comprises the patient care apparatus 4632 and the support shaft 4996 and can be installed or replaced in the field to change the configuration of the particular patient care apparatus 4632 as desired by the user. In one aspect, the support shaft 4996 is installed and rotatably movable in a bore of the transfer device 4631'.

The stationary support platform 4610' of FIG. 24 comprises a mounting pole 4611, a pole link arm 4612, a connecting link arm 4613', and a receiver arm 4852'". In one aspect, the mounting pole 4611 is secured to a nearby surface, such as a wall, of the room or other environment in which the transfer system 4600 is used and is secured by one or more readily-available brackets (not shown). In one aspect, the brackets are of an appropriate size, shape, and material to secure mounting pole and are capable of supporting as much as several hundred pounds or more. In one aspect, a portion of the pole link arm 4612 wraps around a portion of the mounting pole 4611 and is held firmly in place by a clamping force provided by a plurality of fasteners that effectively adjust the roughly circular inside diameter of that portion of the pole link arm 4612 that wraps around and is able to adjustably secure the pole link arm 4612 to the mounting pole 4611 at any one of a number of different positions up and down the mounting pole 4611.

As will be described below in further detail, the connecting link arm 4613' is joined to the pole link arm 4612 by one or more fasteners that allow the connecting link arm 4613' to bend with respect to the pole link arm 4612. The receiver arm 4852'" is joined to the connecting link arm 4613' by one or more fasteners that allow the receiver arm 4852'" to bend with respect to the connecting link arm 4613'. In one aspect, the aforementioned connections between the mounting pole 4611 and the pole link arm 4612, between the pole link arm 4612 and the connecting link arm 4613', and between the receiver arm 4852'" and the connecting link arm 4613' allow a user to articulately move one of a plurality of receivers 4615a',b',c' to any one of an infinite number of positions within a radius defined by the combined length of the pole link arm 4612, the connecting link arm 4613', and the receiver arm 4852'". In one aspect, the receiver arm 4852'" comprises an arm 4840'" and the receiver 4615a'. In one aspect, each of the receivers 4615a',b',c' is frustoconical in shape and can be also described as a cone. In one aspect, a receiver such as the receivers 4615a',b',c' can be incorporated into any one or more components of the transfer system 4600 including, but not limited to the stationary support platform 4610', the mobile support platform 4650", and the mobile stand-alone support platform 4670. In another aspect, each of the receivers 4615a',b',c' is radially symmetric about an axis of the receiver 4615a',b',c' but is not necessarily frustoconical in shape.

The mobile support platform 4650" of FIG. 24 comprises a receiver arm 4652"" and a mobile support adapter 4651. In one aspect, the receiver arm 4652"" comprises an arm 4840"" and the receiver 4615b'. In one aspect, the mobile support platform 4650" is configured to attach to or mount on a mobile platform such as a patient bed, gurney, wheelchair, ambulance, helicopter or other mobile platform between locations within or between medical facilities, such as intensive care rooms, operating rooms, radiology and other imaging facilities, catheterization labs, or between buildings and hospitals. Any mobile platform that comprises a frame of sufficient strength and rigidity can be utilized. In one aspect making use of a hospital bed (not shown), the mobile support platform 4650" is configured to attach to a frame of the hospital bed via attachment of an adapter shaft 4710 or other structure of the mobile support platform 4650" to a portion of the frame of hospital bed.

The mobile stand-alone support platform 4670 of FIG. 24 is substitutable with the stationary support platform 4610' or the mobile support platform 4650" in one aspect including medical environments where a stationary support platform 4610' is not available or desirable. The mobile stand-alone support platform 4670 comprises a base 4672 and a support pole represented by support pole segments 4676a,b mounted to the base 4672 with a pole base 4675. Base 4672 comprises central portion 4673 and a plurality of legs 4674—specifically five legs 4674 in the current aspect although any number of legs 4674 can be present in one aspect and the disclosure of five legs 4674 should not be considering limiting on the current disclosure. Attached to each leg 4674 is a leg support 4671. In one aspect, the leg support is a leg or a caster. In one aspect, the leg support can incorporate the fastener or the fastening elements of the fastener such as the internal or external threads. The fastener can also take the form of one or more weldments or an adhesive. The presence of leg supports 4671 allows the mobile stand-alone support platform 4670 to be transported to and between those aforementioned environments where a stationary or mobile support platform does not exist or is otherwise not available. Once positioned, however, the mobile stand-alone support platform 4670 effectively becomes stationary by locking the leg supports 4671. In one aspect, the locking feature is integral with the leg support although the disclosure of a locking feature that is integral with the leg support should not be considered limiting. Extending from the base 4672 is the support pole represented by the support pole segments 4676. Secured to the top of the support pole segment 4676b is a receiver 4615c' that in one aspect is aligned axially with the support pole segments 4676a,b. In one aspect, no leg supports are required and the base 4672 sits flat on a horizontal surface such as a floor.

In one aspect, one or more parts of the transfer system 4600 include a sacrificial mechanical link—with or without a filler such as the filler 570—to protect at least a portion of the transfer system 4600. In one aspect, the patient care apparatus 4632 comprises a sacrificial mechanical link 2407 between the pole segments 4633a,b or a sacrificial mechanical link 2408 between the pole segments 4633b,c as shown. In one aspect, the offset arm 4634 is part of a sacrificial mechanical link 2406 or comprises a sacrificial mechanical link.

In one aspect, a connection between the connecting link arm 4613' and the receiver arm 4852'" comprises a sacrificial mechanical link 2403. In one aspect, a connection between the receiver arm 4852'" and the receiver 4615a' comprises a sacrificial mechanical link 2409.

In one aspect, a connection between the adapter shaft 4710 and either the receiver arm 4652"" or else an upper portion of the mobile support adapter 4651 of the mobile support platform 4650" comprises a sacrificial mechanical link 2404. In one aspect, a connection between the mobile support adapter 4651 and the receiver arm 4652 comprises a sacrificial mechanical link (not shown). In one aspect, a connection between the receiver arm 4852"" and the receiver 4615b' comprises a sacrificial mechanical link 2410.

In one aspect, the support pole segments 4676a,b of the mobile stand-alone support platform 4670 are connected by a sacrificial mechanical link 2405 proximate to the receiver 4615c'. In one aspect, a connection between the receiver 4615c' and a support pole represented by the support pole segments 4676a,b comprises a sacrificial mechanical link (not shown). In one aspect, a sacrificial mechanical link is included in any one of a number of other locations inside or connected to the transfer system 4600. Disclosure of the sacrificial mechanical links 2403-2410 and their specified locations, however, should not be considered limiting on the current disclosure.

In one aspect, any sacrificial element disclosed herein such as the sacrificial element 150 can be formed from any material that is both structural (during normal operating loads) and deformable (during overloading conditions). For example and without limitation, such a material can include a steel such as low carbon steel or stainless steel; another metal or metal alloy such as brass, bronze, copper, an INCONEL alloy, or any material with similar properties.

In one aspect, a method of using a sacrificial mechanical link such as one of the sacrificial mechanical links 100, 100', 100", 1300, 1800, 2000, 2100, 2300 comprises coupling a corresponding first mechanical element to a corresponding second mechanical element with a corresponding sacrificial element such as one of the sacrificial elements 150, 150', 950, 1450, 1550, 1650, 1700, 1700', 1850, 2050, 2150, 2350. In one aspect, the method further comprises applying a force F to a one of the corresponding first mechanical element and the corresponding second mechanical element, the force F being sufficient to cause deformation of the corresponding sacrificial element.

In one aspect of the aforementioned method of use, the force F causes the corresponding second mechanical element to bend at an angle with respect to an axis of the corresponding first mechanical element. In one aspect, the force F causes a gap distance such as a one of the gap distances G1-G6 between the corresponding first mechanical element and the corresponding second mechanical element to decrease. In one aspect, the sacrificial element is a first sacrificial element, the method further comprising replacing the first sacrificial element with a second sacrificial element without damaging the first mechanical element or the second mechanical element, wherein damaging the first mechanical element or the second mechanical element can include, for example and without limitation, changing the size or shape of any feature of the first mechanical element or the second mechanical element. In one aspect, the method further comprises installing the sacrificial element and the first mechanical element in a transfer system. In one aspect, a one of the first mechanical element 110 and the second mechanical element 120 or its equivalent is removably connected to an end of the sacrificial element 150 or its equivalent with a connecting fastener such as, for example and without limitation, the connecting fastener 160a,b. The connecting fastener 160a,b is configured to prevent disengagement of the sacrificial element 150 with respect to the first mechanical element 110 or the second mechanical element 120 with which the sacrificial element 150 is engaged. The connecting fastener 160a,b can additionally be configured to prevent axial movement of the sacrificial element 150 with respect to the first mechanical element 110 or the second mechanical element 120 to which the sacrificial element 150 is assembled.

One should note that conditional language, such as, among others, "can," "could," "might," or "can," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, can be executed out of order from that shown or discussed, including substantially concurrently or in reverse order, depending on the functionality involved, as would be understood by those reasonably skilled in the art of the present disclosure. Many variations and modifications can be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:
1. A medical system comprising a sacrificial mechanical link for linking a first mechanical element to a second mechanical element, the system comprising:
   a first support pole segment defining a first mechanical element, the first mechanical element comprising a first end and a second end and defining a central axis, the second end of the first mechanical element defining an end surface, the first mechanical element defining a main bore extending into the first mechanical element from the second end of the first mechanical element towards the first end of the first mechanical element, the end surface of the second end of the first mechanical element being radially symmetric about the central axis of the first mechanical element;
   a second support pole segment defining a second mechanical element coupled to the first mechanical element and coupled to and supporting medical equipment defining a structural load, the second mechanical element comprising a first end and a second end and defining a central axis, the first end of the second mechanical element defining an end surface, the second mechanical element defining a main bore extending into the second mechanical element from the first end of the second mechanical element towards the second end of the second mechanical element, the end surface of the first end of the second mechanical element being radially symmetric about the central axis of the second mechanical element;
   a sacrificial element joining the first mechanical element and the second mechanical element; the sacrificial element having a first end received within the main bore of the first mechanical element and a second end received within the main bore of the second mechanical element;
   wherein the first mechanical element is removably connected to the first end of the sacrificial element with a first connecting fastener, the first connecting fastener securably fastened to both the sacrificial element and the first mechanical element and configured to prevent disengagement of the sacrificial element from the first mechanical element;

wherein the second mechanical element is removably connected to the second end of the sacrificial element with a second connecting fastener, the second connecting fastener securably fastened to both the sacrificial element and the second mechanical element and configured to prevent disengagement of the sacrificial element from the second mechanical element, an annular gap being defined axially between the first end of the second mechanical element and the second end of the first mechanical element when the sacrificial mechanical link is in a non-deformed state, the gap configured to allow the second mechanical element to bend about a longitudinal axis of the sacrificial element with respect to the first mechanical element in a deformed state; and wherein the sacrificial element is configured to plastically deform to the deformed state when overloaded and bend to a predetermined maximum deformation angle in the deformed state without damage to either of the first mechanical element or the second mechanical element, second mechanical element configured to continue supporting the medical equipment in the deformed state; and a deformable filler, the filler coupled to the sacrificial element within the gap between the first mechanical element and the second mechanical element of the sacrificial mechanical link.

2. The system of claim 1, wherein a central axis of the sacrificial element is aligned with each of the central axis of the first mechanical element and the central axis of the second mechanical element in the non-deformed state.

3. The system of claim 1, wherein the first mechanical element defines a radius at an intersection of the main bore and the end surface.

4. The system of claim 1, wherein the end surface of the second end of the first mechanical element defines a chamfered edge extending from an outer surface of the first mechanical element angled therewith, wherein the end surface of the first end of the second mechanical element defines a chamfered edge extending from an outer surface of the second mechanical element angled therewith, and wherein each of the chamfered edge of the first mechanical element and the chamfered edge of the second mechanical element is a stop limiting further movement of the second mechanical element relative to the first mechanical element.

5. The system of claim 1, wherein an angle between the central axis of the first mechanical element and the central axis of the second mechanical element defines a maximum deformation angle of at least 5 degrees when the link is in the deformed state.

6. The system of claim 1, wherein a one of the first mechanical element and the second mechanical element comprises an end cavity configured to allow plastic deformation of the sacrificial element without damage to either of the first mechanical element or the second mechanical element, at least a portion of a surface of the end cavity offset axially inward from an axially outermost end of the one of the first mechanical element and the second mechanical element.

7. The system of claim 1, wherein the sacrificial element is cylindrical.

8. The system of claim 1, wherein the second end of the sacrificial element is deformable with respect to the central axis of the first mechanical element to form an angle between a central axis of the second end of the sacrificial element and the central axis of the first mechanical element.

9. The system of claim 1, wherein the filler is positioned between the end surface of the first mechanical element and the end surface of the second mechanical element, a first side of the filler facing the end surface of the first mechanical element and a second side of the filler facing the end surface of the second mechanical element.

10. The system of claim 9, wherein the filler is a ring.

11. The system of claim 9, wherein the filler closes the annular gap between the first mechanical element and the second mechanical element when the link is in a non-deformed state.

12. The system of claim 9, wherein the filler fills the annular gap between the first mechanical element and the second mechanical element to an outer surface of the first mechanical element and to an outer surface of the second mechanical element when the link is in a non-deformed state.

13. The system of claim 9, wherein the filler is formed from an elastomeric material.

14. A method of using a medical system comprising a sacrificial mechanical link, the method comprising:

providing a first support pole segment defining a first mechanical element, the first mechanical element comprising a first end and a second end and defining a central axis, the second end of the first mechanical element defining an end surface, the first mechanical element defining a main bore extending into the first mechanical element from the second end of the first mechanical element towards the first end of the first mechanical element;

providing a second support pole segment defining a second mechanical element, the second mechanical element comprising a first end and a second end and defining a central axis, the first end of the second mechanical element defining an end surface, the second mechanical element defining a main bore extending into the second mechanical element from the first end of the second mechanical element towards the second end of the second mechanical element;

providing a sacrificial element joining the first mechanical element and the second mechanical element; the sacrificial element having a first end received within the main bore of the first mechanical element and coupled thereto with a first connecting fastener and a second end received within the main bore of the second mechanical element and coupled thereto with a second connecting fastener, an annular gap being defined axially between the first end of the second mechanical element and the second end of the first mechanical element when the sacrificial mechanical link is in a non-deformed state, the gap configured to allow the second mechanical element to bend about a longitudinal axis of the sacrificial element with respect to the first mechanical element in a deformed state;

providing a deformable filler, the filler positioned in the gap between the first mechanical element and the second mechanical element, a portion of the filler being compressed when the second mechanical element bends with respect to the first mechanical element;

supporting medical equipment defining a structural load with the second mechanical element;

applying a force to a one of the first mechanical element and the second mechanical element to cause a material forming the sacrificial element to experience internal stresses beyond an elastic limit of the material and thereby experience plastic deformation;

bending the second mechanical element with respect to the first mechanical element from the non-deformed state to the deformed state by a predetermined maximum deformation angle, the sacrificial element experiencing plastic deformation without causing damage to the first mechanical element or the second mechanical element, the deformed state of the sacrificial mechanical link being visible to a user until replacement of the sacrificial element; and continuing to support the medical equipment with the second mechanical element in the deformed state.

15. The method of claim 14, wherein plastic deformation of the sacrificial element is allowed up to but not beyond the predetermined maximum deformation angle.

16. The method of claim 15, wherein the force causes the second mechanical element to bend at an angle with respect to an axis of the first mechanical element.

17. The method of claim 14, wherein the sacrificial element is a first sacrificial element, the method further comprising replacing the first sacrificial element with a second sacrificial element without damaging the first mechanical element or the second mechanical element.

18. The method of claim 14, wherein the second mechanical element is positioned higher than the first mechanical element and the structural load is positioned higher than the second mechanical element.

19. The method of claim 14, wherein the first connecting fastener extends through the first mechanical element and the sacrificial element at an angle approximately orthogonal to an axis of the first mechanical element and an axis of the sacrificial element.

* * * * *